United States Patent
Cheng et al.

(10) Patent No.: US 10,604,541 B2
(45) Date of Patent: Mar. 31, 2020

(54) GLUCOKINASE ACTIVATORS AND METHODS OF USING SAME

(71) Applicant: BRISTOL-MYERS SQUIBB COMPANY, Princeton, NJ (US)

(72) Inventors: Peter Tai Wah Cheng, Princeton, NJ (US); Wei Meng, Pennington, NJ (US); Mark Liu, Las Vegas, NV (US); Bei Wang, Princeton, NJ (US); Rulin Zhao, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/318,173

(22) PCT Filed: Jul. 21, 2017

(86) PCT No.: PCT/US2017/043199
§ 371 (c)(1),
(2) Date: Jan. 16, 2019

(87) PCT Pub. No.: WO2018/017910
PCT Pub. Date: Jan. 25, 2018

(65) Prior Publication Data
US 2019/0233449 A1    Aug. 1, 2019

Related U.S. Application Data

(60) Provisional application No. 62/365,520, filed on Jul. 22, 2016.

(51) Int. Cl.
| C07F 9/40 | (2006.01) |
| A61K 31/675 | (2006.01) |
| A61P 3/00 | (2006.01) |
| C07F 9/6571 | (2006.01) |
| A61P 3/10 | (2006.01) |

(52) U.S. Cl.
CPC ...... *C07F 9/657181* (2013.01); *A61K 31/675* (2013.01); *A61P 3/10* (2018.01); *C07F 9/40* (2013.01); *C07B 2200/13* (2013.01)

(58) Field of Classification Search
CPC ............ C07F 9/40; A61K 31/675; A61P 3/00
USPC .......................................... 548/184; 514/371
See application file for complete search history.

(56) References Cited

U.S. PATENT DOCUMENTS

| 7,910,747 B2 | 3/2011 | Ryono et al. |
| 8,933,024 B2 | 1/2015 | Petry et al. |
| 2012/0004166 A1 | 1/2012 | Keil et al. |

FOREIGN PATENT DOCUMENTS

| WO | WO0166553 A2 | 9/2001 |
| WO | WO2005123132 A2 | 12/2005 |
| WO | WO2007007041 A1 | 1/2007 |
| WO | WO2008005964 A2 | 1/2008 |
| WO | WO2008038018 A1 | 4/2008 |
| WO | WO2008109180 A2 | 9/2008 |
| WO | WO2008154563 A1 | 12/2008 |
| WO | WO2009127546 A1 | 10/2009 |
| WO | WO2010029300 A1 | 3/2010 |
| WO | WO2010107610 A1 | 9/2010 |
| WO | WO2011009845 A1 | 1/2011 |
| WO | WO2012051450 A1 | 4/2012 |
| WO | WO2013037390 A1 | 3/2013 |
| WO | WO2013045413 A1 | 4/2013 |
| WO | WO2016040225 A1 | 3/2016 |

OTHER PUBLICATIONS

Cecil Textbook of Medicine, edited by Bennet, J.C., and Plum F., 20th edition,vol. 1, 1004-1010,, 1996.*
Freshney et al.,Culture of Animal Cells, A Manual of Basic Technique, Alan R. Liss, Inc., 1983, New York, p. 4.*
Dermer et al., Bio/Technology, 1994, 12:320.*
Bebernitz, et al., Investigation of Functionally, Liver, JMedChem, 2009, vol. 52, pp. 6142-6152.
International Search Report, Application No. PCT/US2017/043199, dated Jan. 22, 2019.
Massa, et al., Liver Glucokinase: An Overview, Life, 2011, vol. 63(1), pp. 1-6.

* cited by examiner

*Primary Examiner* — Venkataraman Balasubramanian
(74) *Attorney, Agent, or Firm* — Gary D. Greenblatt

(57) ABSTRACT

A compound, enantiomer, prodrug, diastereomer, or salt is provided which is an activator of the enzyme glucokinase and thus is believed to be useful in as treating diabetes and related diseases, which compound has the structure (I). A method for treating diabetes and related disease employing the compound, enantiomer, prodrug, diastereomer, or salt is also provided.

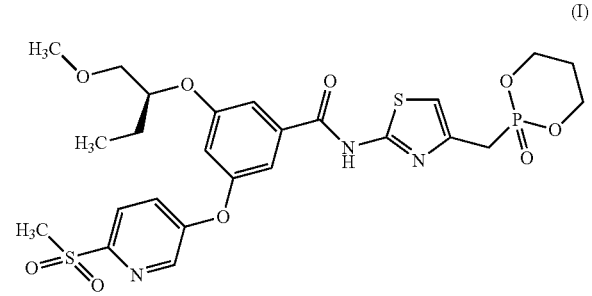

19 Claims, 3 Drawing Sheets

Experimental and simulated powder patterns of 3-(((1S)-1-(methoxymethyl)propyl)oxy)-5-((6-(methylsulfonyl)-3-pyridinyl)oxy)-N-(4-((2-oxido-1,3,2-dioxaphosphinan-2-yl)methyl)-1,3-thiazol-2-yl)benzamide, free base, Form N-1

Thermal analysis of 3-(((1S)-1-(methoxymethyl)propyl)oxy)-5-((6-(methylsulfonyl)-3-pyridinyl)oxy)-N-(4-((2-oxido-1,3,2-dioxaphosphinan-2-yl)methyl)-1,3-thiazol-2-yl)benzamide, free base, Form N-1, crystallized from absolute ethanol Experimental powder pattern of 3-(((1S)-1-(methoxymethyl)propyl)oxy)-5-((6-(methylsulfonyl)-3-pyridinyl)oxy)-N-(4-((2-oxido-1,3,2-dioxaphosphinan-2-yl)methyl)-1,3-thiazol-2-yl)benzamide-Fumaric Acid, Form P-2

GLUCOKINASE ACTIVATORS AND METHODS OF USING SAME

This application is a national phase application under 35 U.S.C. § 371 of International Patent Application No. PCT/US2017/043199, filed Jul. 21, 2017, which claims priority to U.S. Provisional Application No. 62/365,520, filed Jul. 22, 2016, which are expressly incorporated fully herein by reference.

FIELD OF THE INVENTION

The present invention relates to a novel phosphonate compound, enantiomer, prodrug, diastereomer, or salt thereof, which is an activator of the enzyme glucokinase and thus is believed to be useful in treating diseases or disorders activated by the enzyme glucokinase, for example, diabetes, and to a method for treating diseases or disorders activated by the enzyme glucokinase, for example, diabetes, especially Type II diabetes, using such a compound.

BACKGROUND OF THE INVENTION

The enzyme glucokinase (GK), which is mainly found in pancreatic β-cells and liver parenchymal cells, catalyzes the conversion of glucose to glucose-6-phosphate, which is the first step in the metabolism of glucose. Glucokinase is also a rate-controlling enzyme for glucose metabolism in pancreatic β-cells and liver parenchymal cells, which play an important role in whole-body glucose homeostasis.

Liag, Y. et al. (*Biochem. J.*, 309:167-173 (1995)) report the finding that Type II (maturity-onset) diabetes of the young (MODY-2) is caused by loss of function mutations in the glucokinase gene, which suggests that glucokinase also functions as a glucose sensor in humans. Thus, compounds that activate glucokinase and thus increase the sensitivity of the glucokinase sensor system and thereby cause increase in insulin secretion will be useful in the treatment of hyperglycemia and Type II diabetes.

Glucokinase activators have been demonstrated to be effective in enhancing: 1) the effect of glucose on insulin release from isolated rat and human pancreatic islets, and 2) the glucose induction of pancreatic islet glucokinase in isolated cultured rat islets (e.g., Matschinsky, F. M. et al., *Diabetes*, 55:1 (2006), and (Matschinsky, F. M. et al., eds., *Glucokinase and Glycemic Disease, from Basics to Novel Therapeutics*, Karger, publ., Ch. 6, pp. 360-378 (2004)). In diabetic animal model studies, glucokinase activators have been demonstrated to stimulate insulin release, enhance glycogen synthesis and reduce hepatic glucose production in pancreatic clamp studies. Importantly, glucokinase activators have been demonstrated to dose-dependently lower blood glucose levels in different standard animal models of type 2 diabetes, such as the ob/ob mouse, db/db mouse and Zucker fa/fa rat in acute single-dose studies and also effectively improved the glucose excursion in both normal C57/BL6J and ob/ob mice in oral glucose tolerance tests (e.g., in Matschinsky, F. M. et al., eds., *Glucokinase and Glycemic Disease, from Basics to Novel Therapeutics*, Karger, publ., Ch. 6, pp. 360-378 (2004); as well as Fyfe, M. C. et al., *Diabetologia*, 50:1277 (2007)).

Glucokinase activators have also demonstrated antidiabetic efficacy in chronic animal models of type II diabetes. For instance, in a 9-day study in ob/ob mice, a glucokinase activator improved the overall glucose profile while showing comparable antihyperglycemic effects in oral glucose tolerance tests at the beginning and end of the study (Fyfe, M. C. et al., *Diabetologia*, 50:1277 (2007)). In another instance, in a chronic 40-week study, a glucokinase activator prevented the development of hyperglycemia in diet-induced obese mice which were glucose intolerant. The diet-induced obese mice treated with a glucokinase activator showed marked improvement in the glucose excursion in an oral glucose tolerance test at the end of the study relative to the control group Matschinsky, F. M. et al., eds., *Glucokinase and Glycemic Disease, from Basics to Novel Therapeutics*, Karger, publ., Ch. 6, pp. 360-378 (2004)).

Accordingly, compounds that activate glucokinase could demonstrate a wide range of utilities in treating inflammatory, allergic, autoimmune, metabolic, cancer and/or cardiovascular diseases. PCT Publication Nos. WO 2007/007041 A1, WO 2008/005914 A1, WO 2008/154563 A1, WO 2008/005964 A1 (incorporated herein by reference and assigned to present applicant) and WO 2009/018065 A1, disclose compounds that activate glucokinase. The references also disclose various processes to prepare these compounds.

It has also been reported that activation of GK both in the liver and the pancreas could have a profound effect on circulating glucose levels in the diabetic state. However, there are serious concerns that targeting the pancreas could result in the worsening of the diabetic state. In view of this it is desirable to find new compounds that minimize the effects on the pancreas by primarily targeting the liver. (Bebernitz et al., J. Med. Chem. 2009, 52, 6142-6152 and Massa et al., Life, 63(1): 1-6, Jan. 2011).

It is also desirable to find compounds with advantageous and improved characteristics in one or more of the following categories:

(a) pharmaceutical properties (i.e., solubility, permeability, amenability to sustained release formulations);

(b) dosage requirements (e.g., lower dosages and/or once-daily dosing);

(c) factors which decrease blood concentration peak-to-trough characteristics (i.e., clearance and/or volume of distribution);

(d) factors that increase the concentration of active drug at the receptor (i.e., protein binding, volume of distribution, metabolic stability);

(e) factors that decrease the liability for clinical drug-drug interactions (cytochrome P450 enzyme inhibition or induction, such as CYP 2D6 inhibition, see Dresser, G. K. et al., Clin. Pharmacokinet. 38:41-57 (2000), which is hereby incorporated by reference); and (f) factors that decrease the potential for adverse side-effects (e.g., pharmacological selectivity beyond kinase receptors, potential chemical or metabolic reactivity, limited CNS penetration, ion-channel selectivity). It is especially desirable to find compounds having a desirable combination of the aforementioned pharmacological characteristics.

SUMMARY OF THE INVENTION

In accordance with one aspect of the invention, the compound, 3-(((1S)-1-(methoxymethyl)propyl)oxy)-5-((6-(methylsulfonyl)-3-pyridinyl)oxy)-N-(4-((2-oxido-1,3,2-dioxaphosphinan-2-yl)methyl)-1,3-thiazol-2-yl)benzamide, having the formula I, and all stereoisomers thereof, prodrugs thereof, and pharmaceutically acceptable salts thereof, are provided:

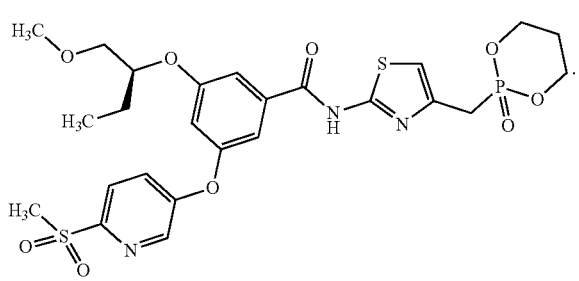

I

The compound, enantiomer, prodrug, diastereomer, or salt thereof, activates or enhances the activity of the enzyme glucokinase. Consequently, the compound, enantiomer, prodrug, diastereomer, or salt thereof, of the present invention may be used in the treatment of multiple diseases or disorders associated with a deficit of glucokinase, such as diabetes and related conditions, microvascular complications associated with diabetes, the macrovascular complications associated with diabetes, cardiovascular diseases, Metabolic Syndrome and its component conditions, and other maladies. Examples of diseases or disorders associated with deficit in activity of the enzyme glucokinase that can be prevented, inhibited, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy, and glaucoma.

The present invention provides for a compound, enantiomer, prodrug, diastereomer, or salt thereof, of formula I, pharmaceutical compositions employing the compound, enantiomer, prodrug, diastereomer, or salt thereof, and for methods of using the compound, enantiomer, prodrug, diastereomer, or salt thereof. In particular, the present invention provides a pharmaceutical composition containing a therapeutically effective amount of the compound, enantiomer, prodrug, diastereomer, or salt thereof, of formula I, alone or in combination with a pharmaceutically acceptable carrier.

Further, in accordance with the present invention, a method is provided for preventing, inhibiting, or treating the progression or onset of diseases or disorders associated with deficit in the activity of the enzyme glucokinase, such as defined above and hereinafter, wherein a therapeutically effective amount of the compound, enantiomer, prodrug, diastereomer, or salt thereof, of formula I is administered to a mammalian, i.e., human, patient in need of treatment.

The compound, enantiomer, prodrug, diastereomer, or salt thereof, of the invention can be used alone, or in combination with one or more other therapeutic agent(s).

Further, the present invention provides a method for preventing, inhibiting, or treating the diseases as defined above and hereinafter, wherein a therapeutically effective amount of a combination of the compound, enantiomer, prodrug, diastereomer, or salt thereof, of formula I and/or at least one other type of therapeutic agent, is administered to a mammalian, i.e., human, patient in need of treatment.

Additionally, the present invention describes a compound, enantiomer, prodrug, diastereomer, or salt thereof, that has a beneficial, preferably a two-fold, more preferably, a three-fold, improvement in liver activity/selectivity, in particular, in vivo glucose reduction, in comparison to compounds previously disclosed in the art, such as those disclosed in PCT Publication No. WO 2008/005964 A1.

The present invention also describes a compound, enantiomer, prodrug, diastereomer, or salt thereof, which is believed to have a beneficial improvement in dosage requirements, for example, improved solubility, in comparison to compounds previously disclosed in the art, such as those disclosed in PCT Publication No. WO 2008/005964 A1.

The present invention also describes a compound, enantiomer, prodrug, diastereomer, or salt thereof, which is believed to have a decrease in liability for clinical drug-drug interactions, for example, cytochrome P450 enzyme inhibition or induction, in comparison to compounds previously disclosed in the art, such as those disclosed in PCT Publication No. WO 2008/005964 A1.

Furthermore, a compound, enantiomer, prodrug, diastereomer, or salt thereof, of the present invention shows unexpected advantages over compounds previously disclosed in the art, such as those disclosed in PCT Publication No. WO 2008/005964 A1. The present compound, enantiomer, prodrug, diastereomer, or salt thereof, has been shown in an assay(s) to have a desirable combination of improvement in liver activity/selectivity and sufficient activity against glucokinase. Such compound should be more useful in the treatment, inhibition or amelioration of one or more diseases or disorders that are discussed herein.

Furthermore, a compound, enantiomer, prodrug, diastereomer, or salt thereof, of the present invention shows unexpected advantages over compounds previously disclosed in the art, such as those disclosed in PCT Publication No. WO 2008/005964 A1. The present compound, enantiomer, prodrug, diastereomer, or salt thereof, has been shown in an assay(s) to have a desirable combination of improvement in liver activity/selectivity, sufficient activity against glucokinase, beneficial improvement in dosage requirements, for example, improved solubility, and a decrease in liability for clinical drug-drug interactions, for example, cytochrome P450 enzyme inhibition or induction. Such compound, enantiomer, prodrug, diastereomer, or salt thereof, should be more useful in the treatment, inhibition or amelioration of one or more diseases or disorders that are discussed herein.

DETAILED DESCRIPTION OF THE INVENTION

In accordance with the present invention, the compound, 3-(((1S)-1-(methoxymethyl)propyl)oxy)-5-((6-(methylsulfonyl)-3-pyridinyl)oxy)-N-(4-((2-oxido-1,3,2-dioxaphosphinan-2-yl)methyl)-1,3-thiazol-2-yl)benzamide, having the formula I, and all stereoisomers thereof, prodrugs thereof, and pharmaceutically acceptable salts thereof, are provided:

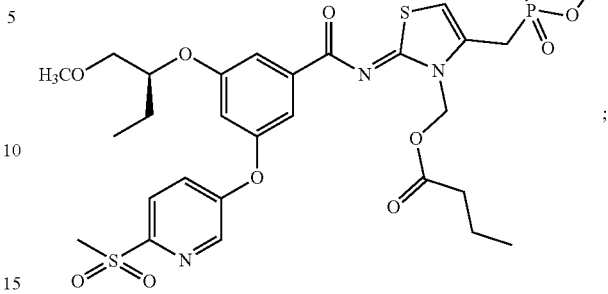

In another embodiment, a compound of the present invention is the salt of the compound of formula I.

In yet another embodiment, a compound of the present invention is the sodium or potassium salt of the compound of formula I.

In yet another embodiment, a compound of the present invention is the sodium salt of the compound of formula I.

In yet another embodiment, a compound of the present invention is the potassium salt of the compound of formula I.

In still yet another embodiment, the compound of the present invention is a crystalline form of the compound of formula I, preferrably the N-1 or P-2 form, more preferably the N-1 form.

In one embodiment, the crystalline form is in substantially pure form.

In one embodiment, the crystalline form of the compound of formula I is characterized by unit cell parameters substantially equal to the following:

Cell Dimensions:
- a=8.0531(2)
- b=13.5078(3)
- c=13.7063(3)
- α=73.091(1)
- β=88.186(1)
- γ=89.881 (1)

Space group: P1

Molecules/asymmetric unit (Z'): 2

Density, calc g-cm$^{-3}$: 1.425

In one embodiment, a compound of the present invention is selected from the group consisting of:

-continued

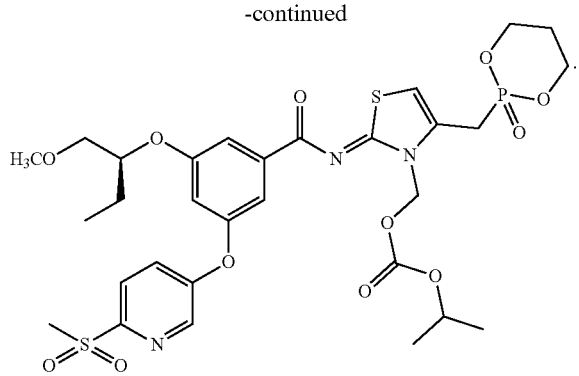

Figure 1:
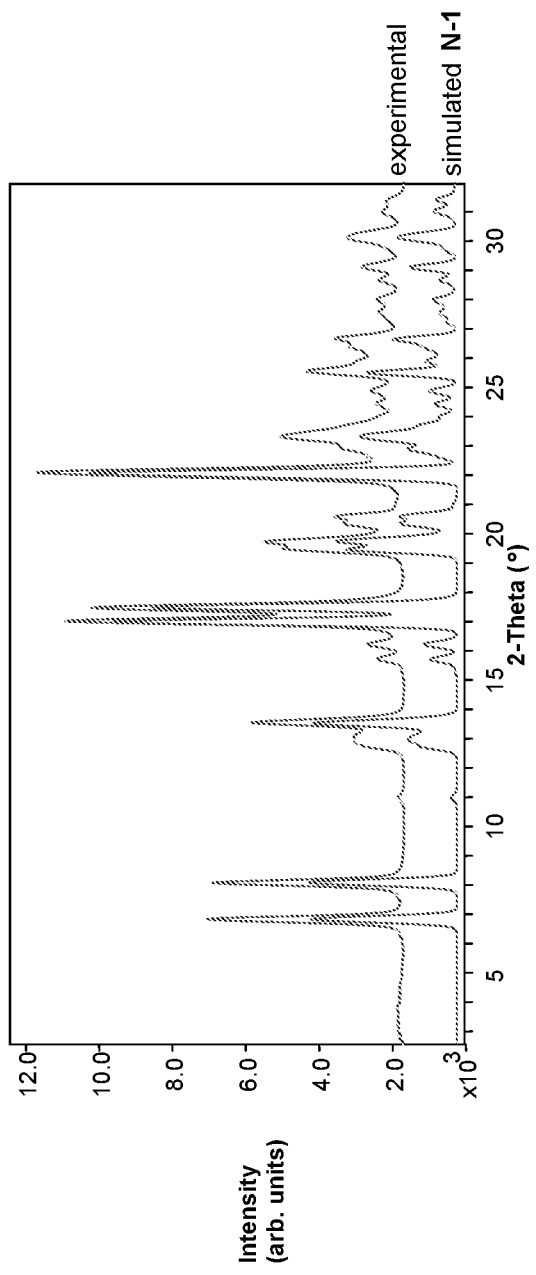
FIG. 1. Experimental and simulated powder patterns of 3-(((1S)-1-(methoxymethyl)propyl)oxy)-5-((6-(methylsulfonyl)-3-pyridinyl)oxy)-N-(4-((2-oxido-1,3,2-dioxaphosphinan-2-yl)methyl)-1,3-thiazol-2-yl)benzamide, free base, Form N-1.
Figure 2:
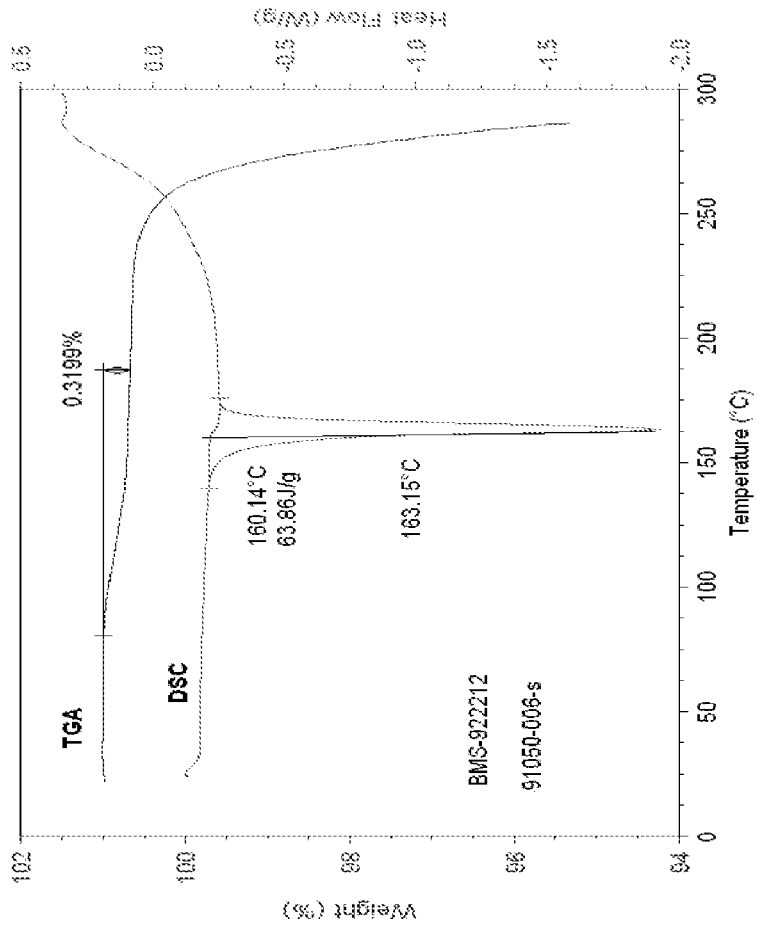
FIG. 2. Thermal analysis of 3-(((1S)-1-(methoxymethyl)propyl)oxy)-5-((6-(methylsulfonyl)-3-pyridinyl)oxy)-N-(4-((2-oxido-1,3,2-dioxaphosphinan-2-yl)methyl)-1,3-thiazol-2-yl)benzamide, free base, Form N-1, crystallized from absolute ethanol.
Figure 3:
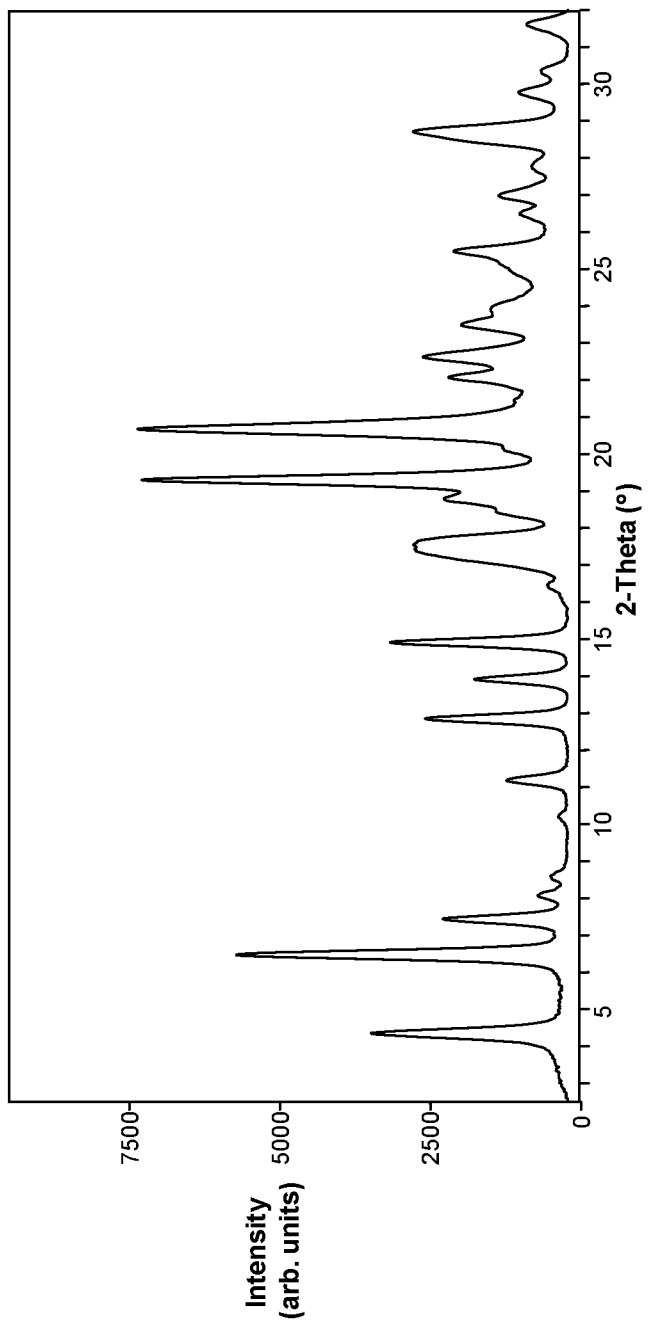
FIG. 3. Experimental powder pattern of 3-(((1S)-1-(methoxymethyl)propyl)oxy)-5-((6-(methylsulfonyl)-3- pyridinyl)oxy)-N-(4-((2-oxido-1,3,2-dioxaphosphinan-2-yl)methyl)-1,3-thiazol-2-yl)benzamide-Fumaric Acid, Form P-2.

In one embodiment, the crystalline form of the compound of formula I is characterized by a powder X-ray diffraction pattern substantially in accordance with that shown in FIG. 1.

In another embodiment, the present invention relates to pharmaceutical compositions which include of a therapeutically effective amount of the compound, enantiomer, prodrug, diastereomer, or salt thereof, of the present invention, alone or, optionally, in combination with a pharmaceutically acceptable carrier and/or one or more other agent(s).

In another embodiment, the present invention relates to methods of enhancing the activity of the enzyme glucokinase which includes the step of administering to a mammalian patient, for example, a human patient, in need thereof a therapeutically effective amount of the compound, enantiomer, prodrug, diastereomer, or salt thereof, of the present invention, alone, or optionally, in combination with at least one other type of therapeutic agent.

In another embodiment, the present invention relates to a method for preventing, inhibiting, or treating the progression or onset of diseases or disorders associated with deficit in the activity of the enzyme glucokinase which includes the step of administering to a mammalian patient, for example, a human patient, in need of prevention, inhibition, or treatment a therapeutically effective amount of the compound, enantiomer, prodrug, diastereomer, or salt thereof, of the present invention, alone, or, optionally, in combination with at least one other type of therapeutic agent.

Examples of diseases or disorders associated with the deficit in activity of the enzyme glucokinase that can be prevented, inhibited, or treated according to the present invention include, but are not limited to, are those diseases or disorders set out above.

In another embodiment, the present invention relates to a method for preventing, inhibiting, or treating the progression or onset of diabetes, hyperglycemia, obesity, dyslipidemia, hypertension, and cognitive impairment which includes the step of administering to a mammalian patient, for example, a human patient, in need of prevention, inhibition, or treatment a therapeutically effective amount of the compound, enantiomer, prodrug, diastereomer, or salt thereof, of the present invention, alone, or, optionally, in combination with at least one other type of therapeutic agent.

In still another embodiment, the present invention relates to a method for preventing, inhibiting, or treating the progression or onset of diabetes, which includes the step of administering to a mammalian patient, for example, a human patient, in need of prevention, inhibition, or treatment a therapeutically effective amount of the compound, enantiomer, prodrug, diastereomer, or salt thereof, of the present invention, alone, or, optionally, in combination at least one other type of therapeutic agent.

In yet still another embodiment, the present invention relates to a method for preventing, inhibiting, or treating the progression or onset of hyperglycemia which includes the step of administering to a mammalian patient, for example, a human patient, in need of prevention, inhibition, or treatment a therapeutically effective amount of the compound, enantiomer, prodrug, diastereomer, or salt thereof, of the present invention, alone, or, optionally, in combination with at least one other type of therapeutic agent.

In another embodiment, the present invention relates to a method for preventing, inhibiting, or treating the progression or onset of obesity which includes the step of administering to a mammalian patient, for example, a human patient, in need of prevention, inhibition, or treatment a therapeutically effective amount of the compound, enantiomer, prodrug, diastereomer, or salt thereof, of the present invention, alone, or, optionally, in combination with at least one other type of therapeutic agent.

In one embodiment, the present invention relates to a method for preventing, inhibiting, or treating the progression or onset of dyslipidemia, which includes the step of administering to a mammalian patient, for example, a human patient, in need of prevention, inhibition, or treatment a therapeutically effective amount of the compound, enantiomer, prodrug, diastereomer, or salt thereof, of the present invention, alone, or, optionally, in combination with at least one other type of therapeutic agent.

Another embodiment of the invention relates to the use of the compound, enantiomer, prodrug, diastereomer, or salt thereof, of formula I in the manufacture of a medicament for the treatment of diabetes.

Another embodiment of the invention relates to the compound, enantiomer, prodrug, diastereomer, or salt thereof, of formula I of the invention for use in therapy in treating diabetes.

Another embodiment of the invention relates to the compound, enantiomer, prodrug, diastereomer, or salt thereof, of formula I of the invention for use in treating diabetes in a mammal.

Another embodiment of the invention relates to the use of the compound, enantiomer, prodrug, diastereomer, or salt thereof, of formula I of the invention in the manufacture of a medicament for treatment of diabetes, in which such treatment comprises a combination with another therapeutic agent, for concurrent or sequential use, in any order.

Another embodiment of the invention relates to the combination of the compound, enantiomer, prodrug, diastereomer, or salt thereof, of formula I of the invention and another therapeutic agent as a medicament for the treatment of diabetes.

Further, the present invention provides for crystalline forms of the compound, enantiomer, prodrug, diastereomer, or salt thereof, of formula I, pharmaceutical compositions employing such crystalline forms, and for methods of using such forms.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

Definitions

The compound of the present invention may be isolated in optically active or racemic forms. It is well known in the art how to prepare optically active forms, such as by resolution of racemic forms or by synthesis from optically active starting materials. All chiral, diastereomeric, and all racemic forms of a structure are intended, unless the specific stereochemistry or isomeric form is specifically indicated.

The phrase "pharmaceutically acceptable" is employed herein to refer to the compound, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compound wherein the parent compound is modified by making acid or base salts thereof.

The terms pharmaceutically acceptable "salt" and "salts" may refer to basic salts formed with inorganic and organic bases. Such salts include ammonium salts; alkali metal salts, such as lithium, sodium, and potassium salts (which are preferred); alkaline earth metal salts, such as calcium and magnesium salts; salts with organic bases, such as amine like salts (e.g., dicyclohexylamine salt, benzathine, N-methyl-D-glucamine, and hydrabamine salts); and salts with amino acids like arginine, lysine, and the like; and zwitterions, the so-called "inner salts." Nontoxic, pharmaceutically acceptable salts are preferred, although other salts are also useful, e.g., in isolating or purifying the product.

The term pharmaceutically acceptable "salt" and "salts" also includes acid addition salts. These are formed, for example, with strong inorganic acids, such as mineral acids, for example sulfuric acid, phosphoric acid, or a hydrohalic acid such as HCl or HBr, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic, or terephthalic acid, such as hydroxycarboxylic acids, for example ascorbic, glycolic, lactic, malic, tartaric, or citric acid, such as amino acids, (for example aspartic or glutamic acid or lysine or arginine), or benzoic acid, or with organic sulfonic acids, such as ($C_1$-$C_4$) alkyl or arylsulfonic acids, which are unsubstituted or substituted, for example by halogen, for example methanesulfonic acid or p-toluenesulfonic acid.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., p. 1418 (1985), the disclosure of which is hereby incorporated by reference.

Any compound that can be converted in vivo to provide the bioactive agent (i.e., the compound of formula I) is a prodrug within the scope and spirit of the invention.

The term "prodrug" denotes a compound which, upon administration to a subject, undergoes chemical conversion by metabolic or chemical processes to yield the compound of formula I, and/or a salt thereof. For example, compounds containing a carboxy group can form physiologically hydrolyzable esters which serve as prodrugs by being hydrolyzed in the body to yield formula compounds per se. Such prodrugs are preferably administered orally since hydrolysis in many instances occurs principally under the influence of the digestive enzymes. Parenteral administration may be used where the ester per se is active, or in those instances where hydrolysis occurs in the blood.

The term "prodrugs" as employed herein includes esters and carbonates formed by reacting the compound of formula I with alkyl, alkoxy, or aryl substituted acylating agents employing procedures known to those skilled in the art to generate acetates, pivalates, methylcarbonates, benzoates, and the like.

Various forms of prodrugs are well known in the art and are described in:
a) Wermuth, C. G. et al., *The Practice of Medicinal Chemistry*, Chapter 31, Academic Press (1996);
b) *Design of Prodrugs*, Bundgaard, H. ed., Elsevier (1985);
c) Bundgaard, H., Chapter 5, "Design and Application of Prodrugs,"*A Textbook of Drug Design and Development*, pp. 113-191, Krosgaard-Larsen, P. et al., eds., Harwood Academic Publishers (1991); and
d) Testa, B. et al., *Hydrolysis in Drug and Prodrug Metabolism*, Wiley-VCH (2003).

Said references are incorporated herein by reference.

The term "tautomer" refers to the compound of the formula I and salts thereof that may exist in its tautomeric form, in which hydrogen atoms are transposed to other parts of the molecules and the chemical bonds between the atoms of the molecules are consequently rearranged. It should be understood that the all tautomeric forms, insofar as they may exist, are included within the invention.

In addition, the compound of formula I may be, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

All stereoisomers of the compound of the instant invention are contemplated, either in admixture or in pure or substantially pure form. The compound of the present invention can exhibit polymorphism. Furthermore, the compound of formula I can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of the compound of the present invention alone or an amount of the combination of the compound of the present invention in combination with other active ingredients effective to treat or prevent diabetes and/or obesity.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The present invention is intended to include all isotopes of atoms occurring in the present compound of the invention. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

The names used herein to characterize a specific form, e.g., "N-1", should not be considered limiting with respect to any other substance possessing similar or identical physical and chemical characteristics, but rather it should be understood that these designations are mere identifiers that should be interpreted according to the characterization information also presented herein.

The present invention provides, at least in part, crystalline forms of the free base of 3-(((1S)-1-(methoxymethyl)propyl)oxy)-5-((6-(methylsulfonyl)-3-pyridinyl)oxy)-N-(4-((2-oxido-1,3,2-dioxaphosphinan-2-yl)methyl)-1,3-thiazol-2-yl)benzamide, as a novel material, in particular in a pharmaceutically acceptable form. In certain preferred embodiments, crystalline forms of the free base are in substantially pure form. Preferred embodiments of crystalline forms of the free base are disclosed in Example 4 as the N-1 and P-2 Forms.

As used herein "polymorph" refers to crystalline forms having the same chemical composition but different spatial arrangements of the molecules, atoms, and/or ions forming the crystal.

As used herein "amorphous" refers to a solid form of a molecule, atom, and/or ions that is not crystalline.

Samples of the crystalline forms may be provided with substantially pure phase homogeneity, indicating the presence of a dominant amount of a single crystalline form and optionally minor amounts of one or more other crystalline forms. The presence of more than one crystalline form in a sample may be determined by techniques such as powder X-ray diffraction (PXRD) or solid state nuclear magnetic resonance spectroscopy (SSNMR). For example, the presence of extra peaks in the comparison of an experimentally measured PXRD pattern with a simulated PXRD pattern may indicate more than one crystalline form in the sample.

The simulated PXRD may be calculated from single crystal X-ray data. See Smith, D. K., "A FORTRAN Program for Calculating X-Ray Powder Diffraction Patterns", Lawrence Radiation Laboratory, Livermore, Calif., UCRL-7196 (April 1963).

Preferably, the crystalline form has substantially pure phase homogeneity as indicated by less than 10%, preferably less than 5%, and more preferably less than 2% of the total peak area in the experimentally measured PXRD pattern arising from the extra peaks that are absent from the simulated PXRD pattern. Most preferred is a crystalline form having substantially pure phase homogeneity with less than 1% of the total peak area in the experimentally measured PXRD pattern arising from the extra peaks that are absent from the simulated PXRD pattern.

Procedures for the preparation of crystalline forms are known in the art. The crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture.

The forms may be characterized and distinguished using single crystal X-ray diffraction, which is based on unit cell and intensity measurements of a single crystal of a form at a fixed analytical temperature. A detailed description of unit cell and intensity analysis is provided in Stout et al., Chapter 3, *X-Ray Structure Determination: A Practical Guide*, MacMillan Co., New York (1968), which is herein incorporated by reference. Alternatively, the unique arrangement of atoms in spatial relation within the crystalline lattice may be characterized according to the observed fractional atomic coordinates. See Stout et al. reference for experimental determination of fractional coordinates for structural analysis. Another means of characterizing the crystalline structure is by powder X-ray diffraction analysis in which the experimental or observed diffraction profile is compared to a simulated profile representing pure powder material, both at the same analytical temperature, and measurements for the subject form characterized as a series of 2θ values and intensities.

The term "negligible weight loss", as employed herein, as characterized by TGA indicates the presence of a neat (non-solvated) crystal form.

In one embodiment of the invention, a crystalline form of 3-(((1S)-1-(methoxymethyl)propyl)oxy)-5-((6-(methylsulfonyl)-3-pyridinyl)oxy)-N-(4-((2-oxido-1,3,2-dioxaphosphinan-2-yl)methyl)-1,3-thiazol-2-yl)benzamide is provided in substantially pure form. This crystalline form may be employed in pharmaceutical compositions which may optionally include one or more other components selected, for example, from the group consisting of excipients, carriers, and one of other active pharmaceutical ingredients or active chemical entities of different molecular structures.

Preferably, the crystalline form has substantially pure phase homogeneity as indicated by less than 10%, preferably less than 5%, and more preferably less than 2% of the total peak area in the experimentally measured PXRD pattern arising from the extra peaks that are absent from the simulated PXRD pattern. Most preferred is a crystalline form having substantially pure phase homogeneity with less than 1% of the total peak area in the experimentally measured PXRD pattern arising from the extra peaks that are absent from the simulated PXRD pattern.

In another embodiment, a composition is provided consisting essentially of the crystalline forms of 3-(((1S)-1-(methoxymethyl)propyl)oxy)-5-((6-(methylsulfonyl)-3-pyridinyl)oxy)-N-(4-((2-oxido-1,3,2-dioxaphosphinan-2-yl)methyl)-1,3-thiazol-2-yl)benzamide. The composition of this embodiment may comprise at least 90 weight % of the form, based on its weight in the composition.

The presence of reaction impurities and/or processing impurities may be determined by analytical techniques known in the art, such as, for example, chromatography, nuclear magnetic resonance spectroscopy, mass spectrometry or infrared spectroscopy.

Crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. High throughput crystallization techniques may be employed to prepare crystalline forms including polymorphs.

Crystals of drugs, including polymorphs, methods of preparation, and characterization of drug crystals are discussed in Byrn, S. R. et al., *Solid-State Chemistry of Drugs*, 2nd Edition, SSCI, West Lafayette, Ind. (1999).

For crystallization techniques that employ solvent, the choice of solvent or solvents is typically dependent upon one or more factors, such as solubility of the compound, crystallization technique, and vapor pressure of the solvent. Combinations of solvents may be employed; for example, the compound may be solubilized into a first solvent to afford a solution, followed by the addition of an antisolvent to decrease the solubility of the compound in the solution and to afford the formation of crystals. An "antisolvent" is a solvent in which the compound has low solubility. Suitable solvents for preparing crystals include polar and nonpolar solvents.

In one method to prepare crystals, 3-(((1S)-1-(methoxymethyl)propyl)oxy)-5-((6-(methylsulfonyl)-3-pyridinyl)oxy)-N-(4-((2-oxido-1,3,2-dioxaphosphinan-2-yl)methyl)-1,3-thiazol-2-yl)benzamide is suspended and/or stirred in a suitable solvent to afford a slurry, which may be heated to promote dissolution. The term "slurry", as used herein, means a saturated solution of the free base, which may also contain an additional amount of the compound to afford a heterogeneous mixture of the compound and a solvent at a given temperature. Suitable solvents in this regard include, for example, polar aprotic solvents and polar protic solvents, and mixtures of two or more of these, as disclosed herein.

Seed crystals may be added to any crystallization mixture to promote crystallization. As will be clear to the skilled artisan, seeding is used as a means of controlling growth of a particular crystalline form or as a means of controlling the particle size distribution of the crystalline product. Accordingly, calculation of the amount of seeds needed depends on the size of the seed available and the desired size of an average product particle as described, for example, in Mullin, J. W. et al., "Programmed cooling of batch crystallizers", *Chemical Engineering Science*, 26:369-377 (1971). In general, seeds of small size are needed to effectively control the growth of crystals in the batch. Seeds of small size may be generated by sieving, milling, or micronizing of larger crystals, or by micro-crystallization of solutions. Care should be taken that milling or micronizing of crystals does not result in any change in crystallinity from the desired crystal form (i.e., change to amorphous or to another polymorph).

A cooled mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as SSNMR, DSC, PXRD, or the like, to assure formation of the preferred crystalline form of the product. The resulting crystalline form is typically produced in an amount of greater than about 70 weight % isolated yield, but preferably greater than 90 weight % based on the weight of 3-(((1S)-1-(methoxymethyl)propyl)oxy)-5-((6-(methylsulfonyl)-3-pyridinyl)oxy)-N-(4-((2-oxido-1,3,2-dioxaphosphinan-2-yl)methyl)-1,3-thiazol-2-yl)benzamide originally employed in the crystallization procedure. The product may be co-milled or passed through a mesh screen to de-lump the product, if necessary.

Crystalline forms may be prepared directly from the reaction medium of the final process step for preparing 3-(((1S)-1-(methoxymethyl)propyl)oxy)-5-((6-(methylsulfonyl)-3-pyridinyl)oxy)-N-(4-((2-oxido-1,3,2-dioxaphosphinan-2-yl)methyl)-1,3-thiazol-2-yl)benzamide. This may be achieved, for example, by employing in the final process step a solvent or mixture of solvents from which the free base may be crystallized. Alternatively, crystalline forms may be obtained by distillation or solvent addition techniques. Suitable solvents for this purpose include any of those solvents described herein, including protic polar solvents, such as alcohols, and aprotic polar solvents, such as ketones.

By way of general guidance, the reaction mixture may be filtered to remove any undesired impurities, inorganic salts, and the like, followed by washing with reaction or crystallization solvent. The resulting solution may be concentrated to remove excess solvent or gaseous constituents. If distillation is employed, the ultimate amount of distillate collected may vary, depending on process factors including, for example, vessel size, stirring capability, and the like. By way of general guidance, the reaction solution may be distilled to about ⅒ the original volume before solvent replacement is carried out. The reaction may be sampled and assayed to determine the extent of the reaction and the wt % product in accordance with standard process techniques. If desired, additional reaction solvent may be added or removed to optimize reaction concentration. Preferably, the final concentration is adjusted to about 50 wt % at which point a slurry typically results.

It may be preferable to add solvents directly to the reaction vessel without distilling the reaction mixture. Although the final concentration may vary depending on desired purity, recovery and the like, the final concentration of the free base in solution is preferably about 4% to about 7%. The reaction mixture may be stirred following solvent addition and simultaneously warmed. By way of illustration, the reaction mixture may be stirred for about 1 hour while warming to about 70° C. The reaction is preferably filtered hot and washed with either the reaction solvent, the solvent added or a combination thereof. Seed crystals may be added to any crystallization solution to initiate crystallization.

The various forms described herein may be distinguishable from one another through the use of various analytical techniques known to one of ordinary skill in the art. Such techniques include, but are not limited to, X-ray powder diffraction (PXRD). Specifically, the forms may be characterized and distinguished using single crystal X-ray diffraction, which is based on unit cell measurements of a single crystal of a given form at a fixed analytical temperature. A detailed description of unit cells is provided in Stout et al. Chapter 3, *X-Ray Structure Determination: A Practical Guide*, MacMillan Co., New York (1968), which is herein incorporated by reference. Alternatively, the unique arrangement of atoms in spatial relation within the crystalline lattice may be characterized according to the observed fractional atomic coordinates. Another means of characterizing the crystalline structure is by powder X-ray diffraction analysis in which the diffraction profile is compared to a simulated profile representing pure powder material, both run at the same analytical temperature, and measurements for the subject form characterized as a series of 2θ values (usually four or more).

Other means of characterizing the form may be used, such as solid state nuclear magnetic resonance (SSNMR) spectroscopy, differential scanning calorimetry (DSC), thermography and gross examination of the crystalline or amorphous morphology. These parameters may also be used in combination to characterize the subject form.

One of ordinary skill in the art will appreciate that an X-ray diffraction pattern may be obtained with a measurement error that is dependent upon the measurement conditions employed. In particular, it is generally known that intensities in an X-ray diffraction pattern may fluctuate depending upon measurement conditions employed and the shape or morphology of the crystal. It should be further understood that relative intensities may also vary depending upon experimental conditions and, accordingly, the exact order of intensity should not be taken into account. Additionally, a measurement error of diffraction angle for a conventional X-ray diffraction pattern is typically about 0.2° or less, preferably about 0.1° (as discussed hereinafter), and such degree of measurement error should be taken into account as pertaining to the aforementioned diffraction angles. Consequently, it is to be understood that the crystal forms of the instant invention are not limited to the crystal forms that provide X-ray diffraction patterns completely identical to the X-ray diffraction patterns depicted in the accompanying Figures disclosed herein. Any crystal forms that provide X-ray diffraction patterns substantially identical to those disclosed in the accompanying Figures fall within the scope of the present invention. The ability to ascertain substantial identities of X-ray diffraction patterns is within the purview of one of ordinary skill in the art.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather is defined by the claims appended hereto.

Abbreviations

DMAP dimethylaminopyridine
DMF N,N-dimethylformamide
EDAC 3-ethyl-3'-(dimethylamino)propyl-carbodiimide hydrochloride (or 1-(3-dimethylaminopropyl)-3-ethylcarbodiimide hydrochloride)
Et$_2$O diethyl ether
EtOH ethanol
EtOAc ethyl acetate
equiv. equivalence
g gram
h hour(s)
HOBT hydroxybenzotriazole
HPLC high pressure liquid chromatography
i-Pr$_2$EtN di(isopropyl)ethylamine
LCMS Liquid Chromatography-Mass Spectroscopy
MeOH methanol
min minute(s)
mL milliliter
mmol millimoles
NaHMDS sodium bis(trimethylsilyl)amide
rt retention time
THF tetrahydrofuran Example 1

3-(((1S)-1-(methoxymethyl)propyl)oxy)-5-((6-(methylsulfonyl)-3-pyridinyl)oxy)-N-(4-((2-oxido-1,3,2-dioxaphosphinan-2-yl)methyl)-1,3-thiazol-2-yl) benzamide

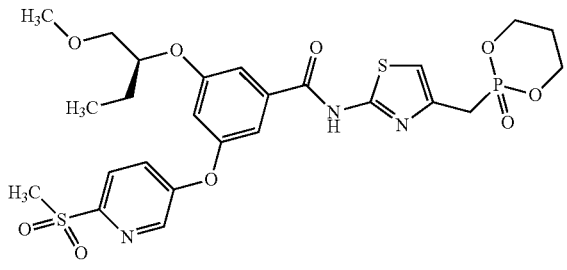 [SMILES: CC[C@@H](COC)Oc1cc(Oc2ccc(S(C)(=O)=O)nc2)cc(C(=O)Nc2nc(CP3(=O)OCCCO3)cs2)c1]

Intermediate 1A: (2R)-1-Methoxy-2-butanol

(Int-1A)

To a stirred suspension of CuI (32.4 g, 170 mmol) in THF (680 mL) under argon at −10° C. was added a solution of CH$_3$MgBr (510 mL, 3.0 M in Et$_2$O, 1532 mmol) dropwise over 30 min. The reaction mixture was stirred for 20 min at −10° C., cooled to −40° C., and (R)-2-(methoxymethyl) oxirane (50 g, 568 mmol) was added dropwise at −40° C. The reaction mixture was allowed to warm to room temperature and stirred at room temperature for 18 h. The reaction mixture was cooled to −40° C. and was carefully quenched with saturated aqueous NH$_4$Cl (500 mL) and water (500 mL). The cooling bath was removed and the reaction mixture was stirred (exposed to air) for 2 h, until a deep blue solution was obtained. The phases were split and the organic phase was extracted with Et$_2$O (500 mL). The combined organic extracts were dried over MgSO$_4$, filtered through a pad of silica gel and the silica gel pad was washed with Et$_2$O (200 mL). The combined filtrates were concentrated in vacuo to provide Intermediate 1A (53.2 g, 90% yield) as a light yellow oil. $^1$H NMR (400 MHz, CDCl$_3$) δ 3.78-3.66 (m, 1H), 3.42 (dd, J=9.3, 2.8 Hz, 1H), 3.39 (s, 3H), 3.25 (dd, J=9.3, 7.7 Hz, 1H), 1.54-1.42 (m, 2H), 0.97 (t, J=7.4 Hz, 3H); $^{13}$C NMR (100 MHz, CDCl$_3$) δ 76.62, 71.0, 58.5, 25.7, 9.5; [α]$^{21.9}_D$ (EtOH, 27.46 mg/mL)=+6.41°; Anal. Calcd. for C$_5$H$_{12}$O$_2$: C, 57.66%; H, 11.61%, found: C, 57.78%; H, 11.19%.

Intermediate 1B: 5-Bromo-2-(methylthio)pyridine

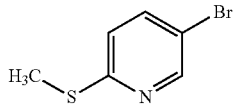

(Int-1B)

To a stirred solution of 2,5-dibromopyridine (180 g, 760 mmol) in DMF (1500 mL) at room temperature under argon was added sodium thiomethoxide (55.9 g, 798 mmol). The reaction mixture was stirred at room temperature for 3 h. Additional sodium thiomethoxide (19.1 g, 272.5 mmol) was added and the reaction mixture was stirred at room temperature for 1 h. The reaction mixture was concentrated in vacuo to ~700 mL at 50° C. The residue was diluted with water (1000 mL) and the product was extracted with Et$_2$O (4×500 mL). The combined organic extracts were washed with saturated aqueous NaHCO$_3$ and brine. The organic phase was dried over MgSO$_4$ and concentrated in vacuo to provide Intermediate 1B (143.8 g, 92% yield) as a white solid. HPLC (YMC CombiScreen ODS-A S-5µ 4.6×50 mm column, detection at 220 nm; flow rate=4 mL/min; continuous gradient from 0% B to 100% B over 4 min+1 min hold time at 100% B where A=90:10:0.2 H$_2$O:MeOH:H$_3$PO$_4$ and B=10:90:0.2 H$_2$O:MeOH:H$_3$PO$_4$) 85.4%, rt=3.14 min; [M+H]$^+$=204.03; $^1$H NMR (300 MHz, CDCl$_3$) δ 8.45 (d, J=1.8 Hz, 1H), 7.54 (dd, J=8.6, 2.4 Hz, 1H), 7.04 (d, J=8.4 Hz, 1H), 2.50 (s, 3H); $^{13}$C NMR (75 MHz, CDCl$_3$) δ 158.6, 150.1, 138.2, 122.6, 115.6, 13.4; Anal. Calcd. for C$_6$H$_6$BrNS: C, 35.31; H, 2.96; N, 6.86; Found: C, 35.25%; H, 2.94%; N, 6.78%.

Intermediate 1C: 5-Bromo-2-(methylsulfonyl)pyridine

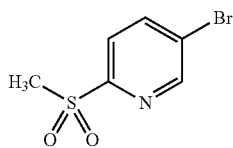

(Int-1C)

To a stirred solution of Intermediate 1B (143 g, 701 mmol) in water (1200 mL) at room temperature was added OXONE® monopersulfate (1077 g, 1752 mmol). The reaction mixture was stirred for 18 h at room temperature. The reaction mixture was filtered and the filter cake was washed with water and dried in vacuo to provide Intermediate 1C (148.5 g, 90% yield) as a white solid. HPLC (YMC CombiScreen ODS-A S-5µ 4.6×50 mm column, detection at 220 nm; flow rate=4 mL/min; continuous gradient from 0% B to 100% B over 4 min+1 min hold time at 100% B where A=90:10:0.2 H$_2$O:MeOH:H$_3$PO$_4$ and B=10:90:0.2 H$_2$O: MeOH:H$_3$PO$_4$) 98.7%, rt=1.75 min; [M+H]$^+$=237.99; $^1$H NMR (300 MHz, CDCl$_3$) δ 8.76 (dd, J=2.2, 0.7 Hz, 1H), 8.08 (dd, J=8.4, 2.2 Hz, 1H), 7.95 (d, J=8.1 Hz, 1H), 3.20 (s, 3H); $^{13}$C NMR (75 MHz; CDCl$_3$) δ 156.21, 151.1, 140.8, 125.51, 124.82, 122.4, 40.0; Anal. Calcd. for C$_6$H$_6$BrNO$_2$S: C, 30.52; H, 2.56; N, 5.93; Found: C, 30.52%; H, 2.56%; N, 5.93%.

Intermediate 1D: Methyl 3-hydroxy-5-[[6-(methylsulfonyl)pyridin-3-yl]oxy]benzoate

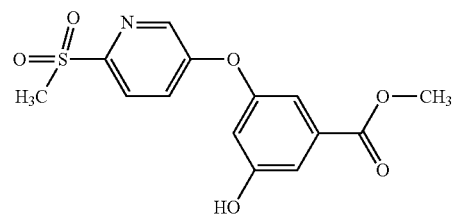

(Int-1D)

To a stirred solution of methyl 3,5-dihydroxybenzoate (42.7 g, 254 mmol) in DMF (400 mL) was added Intermediate 1C (30 g, 127 mmol) and Cs$_2$CO$_3$ (53.8 g, 165 mmol) and the reaction mixture was stirred at 110° C. for 18 h. The reaction mixture was cooled to room temperature, diluted with water (200 mL) and saturated aqueous NaHCO$_3$ (200 mL), stirred at room temperature for 15 min and washed with EtOAc (2×250 mL). The aqueous phase was cooled in an ice/water bath, acidified to pH=3 with concentrated HCl and extracted with EtOAc (2×250 mL). The combined organic extracts were dried over MgSO$_4$ and concentrated in vacuo to provide a brown oil. The oil was chromatographed (SiO$_2$; 1000 g; continuous gradient from 0% EtOAc/hexane to 80% EtOAC/hexane) to provide Intermediate 1D (18.99 g, 46.2% yield) as a white solid. HPLC (YMC CombiScreen ODS-A S-5µ 4.6×50 mm column, detection at 220 nm; flow rate=4 mL/min; continuous gradient from 0% B to 100% B over 4 min+1 min hold time at 100% B where A=90:10:0.2 H$_2$O:MeOH:H$_3$PO$_4$ and B=10:90:0.2 H$_2$O:MeOH:H$_3$PO$_4$) 90.0%, rt=2.55 min; [M+H]$^+$=324.1; $^1$H NMR (500 MHz, CDCl$_3$) δ 8.48 (d, J=2.5 Hz, 1H), 8.09 (d, J=8.5 Hz, 1H), 7.48-7.44 (m, 2H), 7.31 (s, 1H), 6.84 (t, J=2.3 Hz, 1H), 3.94 (s, 3H), 3.26 (s, 3H); $^{13}$C NMR (75 MHz, CDCl$_3$) δ 166.1, 158.1, 156.8, 155.4, 151.2, 140.8, 133.0, 125.2, 122.9, 114.0, 112.4, 112.0, 52.6, 40.5; Anal. Calcd. for C$_{14}$H$_{13}$NO$_6$S: C, 52.01; H, 4.05; N, 4.33; Found: C, 51.94%; H, 3.90%; N, 4.29%.

Intermediate 1E: (S)-3-((1-Methoxybutan-2-yl)oxy)-5-((6-(methylsulfonyl)pyridin-3-yl)oxy)benzoic acid

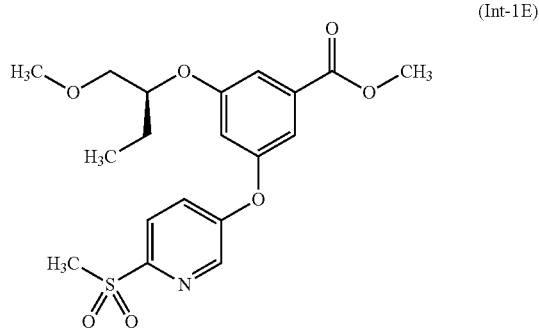
(Int-1E)

To a stirred solution of Intermediate 1D (23.8 g, 73.6 mmol), Intermediate 1A 10.81 g, 96 mmol) and triphenylphosphine (23.17 g, 88 mmol) in THF (200 mL) under argon at 0° C. was added di-tert-butylazodicarboxylate (25.4 g, 110 mmol) drop wise. The reaction mixture was allowed to warm to room temperature and was stirred at room temperature for 15 h. The reaction mixture was diluted with EtOAc, washed sequentially with water, 1N aqueous HCl and brine, dried over anhydrous magnesium sulfate and concentrated in vacuo. The residue was chromatographed ($SiO_2$; 330 g; continuous gradient from 0% EtOAc/hexane to 50% EtOAC/hexane) to provide Intermediate 1E (25.3 g, 84% yield) as a colorless oil. HPLC (YMC CombiScreen ODS-A S-5µ 4.6×50 mm column, detection at 220 nm; flow rate=4 mL/min; continuous gradient from 0% B to 100% B over 4 min+1 min hold time at 100% B where A=90:10:0.2 $H_2O$:MeOH:$H_3PO_4$ and B=10:90:0.2 $H_2O$:MeOH:$H_3PO_4$) 92%, rt=3.32 min; 99.8% ee (SFC; Chiralpak AD-H, 0.46×25 cm, 5 µm column, detection at 200-400 nm; flow rate=3 mL/min; isocratic 70/30 $CO_2$/MeOH mobile phase; 100 bars pressure); $[M+H]^+$=410.1; $^1$H NMR (300 MHz, $CDCl_3$) δ 8.41 (d, J=2.6 Hz, 1H), 8.00 (d, J=8.8 Hz, 1H), 7.46 (dd, J=2.2, 1.5 Hz, 1H), 7.38 (dd, J=8.8, 2.6 Hz, 1H), 7.24 (dd, J=2.2, 1.5 Hz, 1H), 6.86 (t, J=2.4 Hz, 1H), 4.40-4.26 (m, 1H), 3.85 (s, 3H), 3.51 (dd, J=5.1, 2.2 Hz, 2H), 3.32 (s, 3H), 3.17 (s, 3H), 1.75-1.63 (m, 2H), 0.94 (t, J=7.5 Hz, 3H); $^{13}$C NMR (75 MHz, $CDCl_3$) δ 165.7, 160.3, 156.6, 155.5, 151.8, 140.8, 133.1, 125.2, 122.8, 113.7, 112.8, 112.6, 79.2, 74.0, 59.3, 52.4, 40.4, 24.2, 9.5; $[\alpha]^{23.4}_D$ (EtOH, 5.73 mg/mL)=−21.75°; Anal. Calcd. for $C_{19}H_{23}NO_7S$: C, 55.73%; H, 5.66%; N, 3.42%; Found: C, 55.92%; H, 5.46%; N, 3.41%.

Intermediate 1F: (S)-3-((1-Methoxybutan-2-yl)oxy)-5-((6-(methylsulfonyl)pyridin-3-yl)oxy)benzoic acid

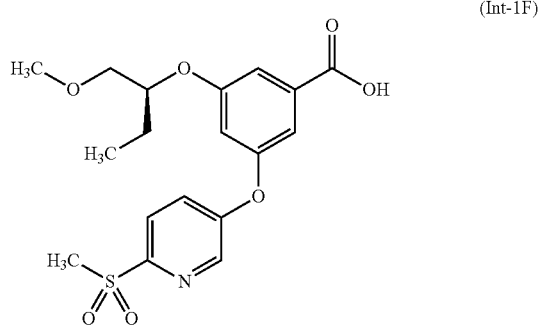 [SMILES: CC[C@@H](COC)Oc1cc(Oc2ccc(S(C)(=O)=O)nc2)cc(C(=O)O)c1]
(Int-1F)

A stirred solution of Intermediate 1E (155 g, 379 mmol) and LiOH.$H_2O$ (27.2 g, 1136 mmol) in THF (1500 mL)/$H_2O$ (500 mL) was stirred for 18 h at room temperature. The reaction mixture was concentrated in vacuo to remove the THF and the remaining aqueous solution was washed with $Et_2O$ (2×40 mL), acidified to pH 2 with 1N aqueous HCl and then extracted with EtOAc (2×40 mL). The combined organic extracts were washed with water (50 mL), dried over $Na_2SO_4$ and concentrated in vacuo to provide the crude product as a colorless oil. This oil was recrystallized from EtOAc/hexane (4 times) and from MeOH/$H_2O$ (4 times) to provide a white solid (100.4 g). The combined mother liquors from these recrystallizations were concentrated in vacuo to provide a colorless oil that was recrystallized from EtOAc/hexane (4 times) and from MeOH/$H_2O$ (4 times) to provide additional white solid (21.5 g). All the recrystallized material was combined to provide Intermediate 1F (121.9 g, 80.6% yield) as a white solid. HPLC (YMC CombiScreen ODS-A S-5µ 4.6×50 mm column, detection at 220 nm; flow rate=4 mL/min; continuous gradient from 0% B to 100% B over 4 min+1 min hold time at 100% B where A=90:10:0.2 $H_2O$:MeOH:$H_3PO_4$ and B=10:90:0.2 $H_2O$:MeOH:$H_3PO_4$) 99%, rt=3.02 min; $[M+H]^+$=396.1; $^1$H NMR (400 MHz, $CDCl_3$) δ 8.48 (d, J=2.2 Hz, 1H), 8.08 (dd, J=8.6, 0.4 Hz, 1H), 7.59-7.56 (m, 1H), 7.45 (dd, J=8.7, 2.8 Hz, 1H), 7.38-7.35 (m, 1H), 6.96 (t, J=2.3 Hz, 1H), 4.48-4.35 (m, 1H), 3.63-3.55 (m, 2H), 3.40 (s, 3H), 3.24 (s, 3H), 1.82-1.69 (m, 2H), 1.00 (t, J=7.5 Hz, 3H); $^{13}$C NMR (100 MHz, $CDCl_3$) δ: 170.4, 160.5, 156.7, 155.6, 151.6, 140.8, 132.2, 125.2, 122.9, 114.2, 113.4, 79.3, 74.0, 59.3, 40.4, 24.1, 9.6; $[\alpha]^{23.4}_D$ ($CHCl_3$, 3.84 mg/mL)=−20.48°; Anal. Calcd. for $C_{18}H_{21}NO_7S$: C, 54.67%; H, 5.35%; N, 3.54%; Found: C, 54.44%; H, 5.30%; N, 3.49%.

Intermediate 1G: 4-(Chloromethyl)thiazol-2-amine hydrochloride

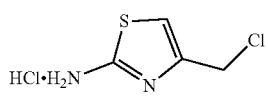
(Int-1G)

To a stirred 25° C. solution of 1,3-dichloropropan-2-one (35 g, 276 mmol) in acetone (150 mL) was added dropwise a 25° C. solution of thiourea (20.98 g, 276 mmol) in acetone (800 mL). The resulting mixture was stirred at room temperature for 72 h. The reaction mixture was filtered and the filter cake was washed with cold acetone. The filter cake was dried under vacuum to provide Intermediate 1G (49.6 g, 97% yield) as a white solid. HPLC (YMC CombiScreen ODS-A S-5µ 4.6×50 mm column, detection at 220 nm; flow rate=4 mL/min; continuous gradient from 0% B to 100% B over 4 min+1 min hold time at 100% B where A=90:10:0.2 $H_2O$:MeOH:$H_3PO_4$ and B=10:90:0.2 $H_2O$:MeOH:$H_3PO_4$) 91%, rt=0.19 min; $[M+H]^+$=148.9; $^1$H NMR (400 MHz, DMSO-$d_6$) δ 7.01 (s, 1H), 4.73 (s, 2H); $^{13}$C NMR (100 MHz, DMSO-$d_6$) δ: 170.4, 135.9, 108.3, 37.6; Anal. Calcd. for $C_4H_6Cl_2N_2S$: C, 25.96%; H, 3.27%; N, 15.14%; Found: C, 26.2%; H, 3.46%; N, 15.22%.

Intermediate 1H: tert-butyl [4-(chloromethyl)thiazol-2-yl]carbamate

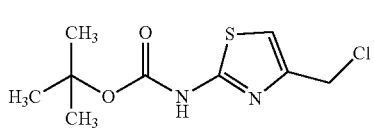

To a stirred 0° C. mixture of Intermediate 1G (50 g, 270 mmol) in water (100 mL) and $CH_2Cl_2$ (210 mL) was added $NaHCO_3$ (45.3 g, 539 mmol) portion wise. The reaction mixture was stirred at 0° C. for 15 min. NaCl (21.5 g) was added to saturate the aqueous layer and the mixture was stirred at 0° C. for 5 min. The aqueous phase was extracted with $CH_2Cl_2$ (10×210 mL) and the combined organic extracts were concentrated in vacuo to about 800 mL. To this solution were added di-tert-butyl dicarbonate (64 g, 293 mmol) and DMAP (1.65 g, 13.5 mmol). The reaction mixture was stirred at room temperature for 18 h. The reaction mixture was washed with 1N aqueous HCl (2×260 mL), dried over $MgSO_4$ and concentrated in vacuo to provide Intermediate 1H (61.9 g, 97% yield) as a white solid. HPLC (YMC CombiScreen ODS-A S-5μ 4.6×50 mm column, detection at 220 nm; flow rate=4 mL/min; continuous gradient from 0% B to 100% B over 4 min+1 min hold time at 100% B where A=90:10:0.2 $H_2O$:MeOH:$H_3PO_4$ and B=10:90:0.2 $H_2O$:MeOH:$H_3PO_4$) 92%, rt=3.10 min; $[M+H]^+$=249.1; $^1$H NMR (400 MHz, $CDCl_3$) δ 6.89 (s, 1H), 4.65 (s, 2H), 1.57 (s, 9H); $^{13}$C NMR (100 MHz, $CDCl_3$) δ: 161.9, 152.6, 146.6, 110.7, 83.0, 40.9, 28.2; Anal. Calcd. for $C_9H_{13}ClN_2O_2S$: C, 43.46%; H, 5.27%; N, 11.26%; Found: C, 43.84%; H, 5.25%; N, 11.22%.

Intermediate 1I: 1,3,2-Dioxaphosphorinane 2-oxide

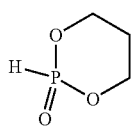

A solution of diethyl phosphonate (555 g, 4019 mmol) and propane-1,3-diol (306 g, 4019 mmol) under argon was stirred at 130° C. for 6 h. The reaction vessel was fitted with a short path distillation head and a receiver. A vacuum of 140 mm Hg was slowly applied. The reaction mixture was stirred at 140 mm Hg and 130° C. until the EtOH distillation ceased (~4 h). The reaction mixture was allowed to cool to 100° C., a vacuum of 50 mm Hg was slowly applied and the reaction mixture was stirred at 50 mm Hg and 100° C. until the distillation ceased (1 h). The vacuum was slowly reduced to 0.5 mm Hg and the title compound was isolated by distillation at 0.5 mm Hg and 120-125° C. as a clear oil. This oil solidified on standing to provide Intermediate 1I as a white solid (443.5 g, 90% yield). $^1$H NMR (400 MHz, $CDCl_3$) δ: 7.06 (d, J=676.1 Hz, 1H), 4.20-4.37 (m, 4H), 2.04-2.20 (m, 1H), 1.60-1.71 (m, 1H); $^{13}$C NMR (100 MHz, $CDCl_3$) δ 67.2 (d, J=6.9 Hz), 26.0 (d, J=8.4 Hz); $^{31}$P NMR (160 MHz, $CDCl_3$) δ 4.4 (d, J=668.8 Hz); Anal. Calcd. for $C_3H_7O_3P$: C, 29.52%; H, 5.78%; Found: C, 29.37%; H, 5.78%.

Intermediate 1J: tert-Butyl (4-((2-oxido-1,3,2-dioxaphosphinan-2-yl)methyl)thiazol-2-yl)carbamate

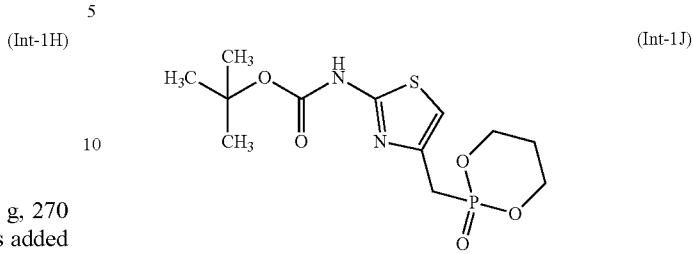

To a stirred solution of NaHMDS in THF (450 mL of a 1M solution; 450 mmol) at 0° C. was added dropwise a solution of Intermediate 1I (62.8 g, 515 mmol) in THF (65 mL) and the resultant slurry was stirred at 0° C. for 45 min. A solution of the Intermediate H compound (32 g, 129 mmol) in THF (98 mL) was added dropwise at 0° C. The reaction mixture was stirred at 0° C. for 1 h, after which the cooling bath was removed, and the reaction mixture was stirred for an additional 6 h at room temperature. The reaction mixture was cooled to 0° C. and the reaction was slowly quenched with saturated aqueous $NH_4Cl$ (300 mL). The organic phase was washed with brine (300 mL), dried over $MgSO_4$ and concentrated in vacuo to a pale yellow foam that was triturated with EtOAc (200 mL), filtered, washed with EtOAc (25 mL) and dried in vacuo to provide Intermediate 1J as a white solid (13.8 g). The combined EtOAc washes were concentrated in vacuo to provide a yellow foam that was chromatographed ($SiO_2$; 330 g; continuous gradient from 0% MeOH/EtOAc to 6% MeOH/EtOAc followed by a continuous gradient from 6% MeOH/$CH_2Cl_2$ to 20% MeOH/$CH_2Cl_2$) to provide a white solid (10.0 g). These white solids were combined to provide Intermediate 1J (23.8 g, 55.4% yield) as a white solid. HPLC (YMC CombiScreen ODS-A S-5μ 4.6×50 mm column, detection at 220 nm; flow rate=4 mL/min; continuous gradient from 0% B to 100% B over 4 min+1 min hold time at 100% B where A=90:10:0.2 $H_2O$:MeOH:$H_3PO_4$ and B=10:90:0.2 $H_2O$:MeOH:$H_3PO_4$) 98%, rt=2.57 min; $[M+H]^+$=335.1; $^1$H NMR (400 MHz, $CDCl_3$) δ 6.82 (d, J=4.2 Hz, 1H), 4.57-4.42 (m, 2H), 4.36-4.20 (m, 2H), 3.37 (d, J=20.9 Hz, 2H), 2.10-2.01 (m, 1H), 1.99-1.89 (m, 1H), 1.56 (s, 9H); $^{13}$C NMR (100 MHz, $CDCl_3$) δ: 161.2, 152.5, 140.4, 109.6, 82.5, 66.8, 29.5, 28.0, 26.0; $^{31}$P NMR (160 MHz, $CDCl_3$) δ 19.4; Anal. Calcd. for $C_{12}H_{19}N_2O_5PS$: C, 43.11%; H, 5.72%; N, 8.37%; Found: C, 43.36%; H, 5.45%; N, 8.38%.

Intermediate 1K: 2-((2-Aminothiazol-4-yl)methyl)-1,3,2-dioxaphosphinane 2-oxide methanesulfonate

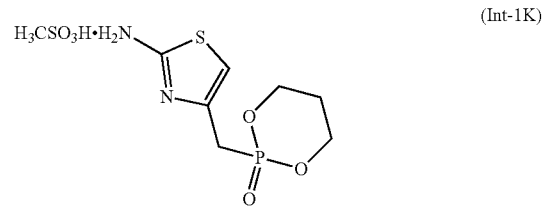

To stirred suspension of Intermediate 1J (42 g, 126 mmol) in acetonitrile (200 mL) was added methanesulfonic acid (15.1 g, 157 mmol) and the reaction mixture was stirred at 55° C. for 12 h. At 55° C., tert-butyl methyl ether (200 mL) was added; the reaction mixture was cooled to 0° C. and stirred at 0° for 3 h. The mixture was filtered and the solids were washed with cold 1:1 acetonitrile: tert-butyl methyl ether (50 mL), then dried in vacuo at 40° C. to provide Intermediate 1K (41 g, 98.5% yield) as an off-white solid. HPLC (YMC CombiScreen ODS-A S-5μ 4.6×50 mm column, detection at 220 nm; flow rate=4 mL/min; continuous gradient from 0% B to 100% B over 4 min+1 min hold time at 100% B where A=90:10:0.2 $H_2O$:MeOH:$H_3PO_4$ and B=10:90:0.2 $H_2O$:MeOH:$H_3PO_4$) 99%, rt=0.19 min; [M+H]$^+$=235.1; $^1$H NMR (500 MHz, DMSO-$d_6$) δ 6.90 (s, 3H), 6.31 (d, J=4.1 Hz, 1H), 4.42-4.34 (m, 2H), 4.34-4.25 (m, 2H), 3.21 (d, J=20.1 Hz, 2H), 2.10-1.99 (m, 1H), 1.78-1.70 (m, 1H); $^{13}$C NMR (100 MHz, CD$_3$OD) δ: 172.4, 131.8, 106.4, 69.8, 39.6, 27.5, 25.9, 24.5; $^{31}$P NMR (160 MHz, DMSO-$d_6$) δ 15.8; Anal. Calcd. for $C_8H_{15}N_2O_6PS_2$: C, 29.09%; H, 4.58%; N, 8.48%; P, 9.38%; S, 19.41%; Found: C, 29.44%; H, 4.79%; N, 8.48%; P, 8.67%; S, 17.78%.

Example 1

To a stirred suspension of Intermediate 1K (23.08 g, 73.4 mmol) in DMF (160 mL) was added i-Pr$_2$EtN (15.8 g, 122 mmol) and the reaction mixture was heated to 70° C. Intermediate 1F (24.2 g, 61.2 mmol), HOBT hydrate (10.78 g, 70.4 mmol) and EDAC (16.42 g, 86 mmol) were added to the 70° C. reaction mixture. The reaction mixture was stirred at 80° C. for 25 min. The reaction mixture was cooled to room temperature, diluted with EtOAc (600 mL), washed sequentially with $H_2O$ (250 mL), saturated aqueous NaHCO$_3$ (2×250 mL), 1N aqueous HCl (250 mL) and brine (250 mL), dried over Na$_2$SO$_4$ and concentrated in vacuo to provide a white foam (40 g). The white foam was recrystallized from EtOH (350 mL) to provide Example 1 (34.4 g, 92% yield) as a white solid. Analytical HPLC (YMC CombiScreen ODS-A S-5μ 4.6×50 mm column, detection at 220 nm; flow rate=4 mL/min; continuous gradient from 0% B to 100% B over 4 min+1 min hold time at 100% B where A=90:10:0.2 $H_2O$:MeOH:$H_3PO_4$ and B=10:90:0.2 $H_2O$:MeOH:$H_3PO_4$) 99.6%, rt=2.57 min; ≥99.0% ee (SFC; Chiralcel OJ-H, 0.46×25 cm, 5 μm column, detection at 200 nm; flow rate=3 mL/min; isocratic 80/20 CO$_2$/MeCN:iPrOH (1:1) mobile phase; 150 bars pressure); [M+H]$^+$=612.2; $^1$H NMR (400 MHz, CDCl$_3$) δ: 11.74 (br. s, 1H), 8.51 (d, 1H), 8.09 (d, 1H), 7.61-7.68 (m, 1H), 7.54 (m, 1H), 7.46-7.50 (m, 1H), 6.93 (m, 1H), 6.87 (d, 1H), 4.46-4.58 (m, 1H), 4.28-4.41 (m, 2H), 4.03-4.19 (m, 2H), 3.69 (d, 2H), 3.58-3.62 (m, 2H), 3.39 (s, 3H), 3.24 (s, 3H), 1.89-1.97 (m, 2H), 1.71-1.83 (m, 2H), 1.60-1.71 (m, 1H), 1.00 (m, 3H); $^{13}$C NMR (100 MHz, CD$_3$OD) δ: 166.0, 162.2, 160.2, 158.3, 157.6, 153.3, 142.4, 142.2, 136.8, 127.2, 124.3, 113.6, 113.0, 112.8, 112.4, 80.4, 75.1, 69.3, 59.6, 40.8, 29.1, 28.1, 27.5, 25.3, 9.9; $^{31}$P NMR (160 MHz, CD$_3$OD) δ: 21.11; [α]$^{21.9}_D$ (MeCN, 4.19 mg/mL)=−18.4°; Anal. Calcd. for $C_{25}H_{30}N_3O_9PS_2$: C, 49.10%; H, 4.95%; N, 6.86%; Found: C, 49.09%; H, 4.96%; N, 6.87%.

Alternatively, Example 1 can prepared according to the following reaction scheme:

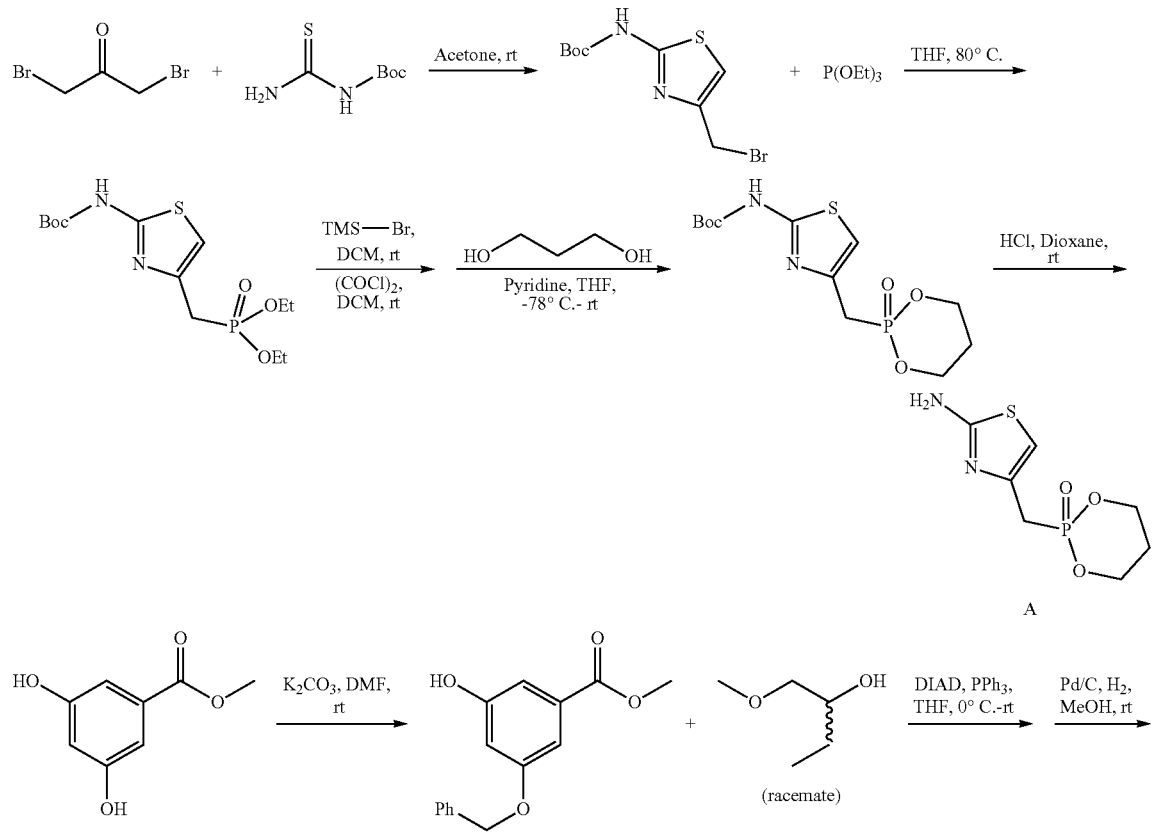

-continued

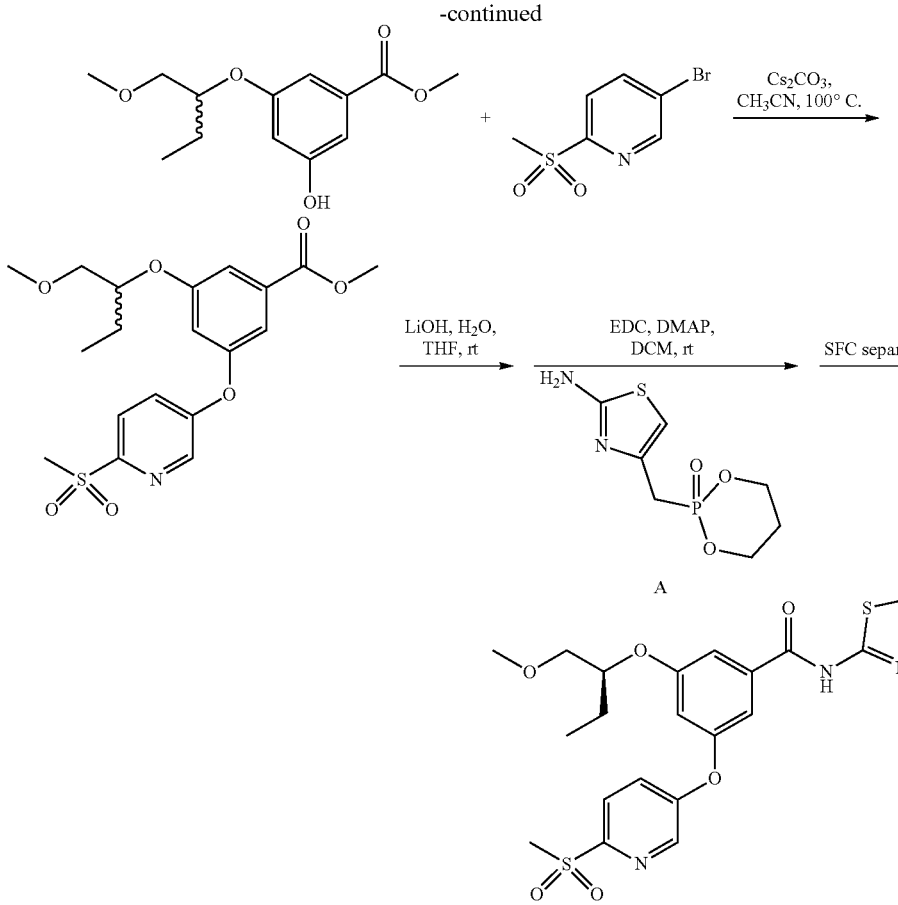

Example 2

Sodium Salt of 3-(((1S)-1-(methoxymethyl)propyl)oxy)-5-((6-(methylsulfonyl)-3-pyridinyl)oxy)-N-(4-((2-oxido-1,3,2-dioxaphosphinan-2-yl)methyl)-1,3-thiazol-2-yl)benzamide

Intermediate 2A: Sodium, 4-pentylphenolate (Int-2A)

4-Pentylphenol (3.604 g, 21.94 mmol) was dissolved in MeOH (10 mL) in a 100 mL 1 neck pear shaped flask that was equipped with a magnetic stirrer and an argon inlet. A solution of NaOH (0.878 g, 21.94 mmol) in a mixture of MeOH (24 mL) and water (6 mL) was added. The reaction mixture was stirred at room temperature for 15 min. The reaction mixture was concentrated in vacuo to a semisolid that was dried at 100° C. under vacuum overnight to provide a white solid. The white solid was slurried on petroleum ether (40 mL), the slurry was filtered and the filter cake was washed with petroleum ether (2×10 mL). The filter cake was dried under vacuum to provide Intermediate 2A (3.9424 g, 96% yield) as a white solid. $^1$H NMR (400 MHz, DMSO-$d_6$) δ 6.52 (d, J=8.3 Hz, 2H), 5.99 (d, J=8.2 Hz, 2H), 2.25 (t, J=7.4 Hz, 2H), 1.41 (quin, J=7.4 Hz, 2H), 1.33-1.15 (m, 4H), 0.84 (t, J=6.9 Hz, 3H).

Example 2

Example 1 (11.024 g, 18.02 mmol) was dissolved in THF (50 mL) in a 250 mL 1 neck flask that was equipped with a magnetic stirrer, a reflux condenser and an argon inlet. A solution of Intermediate 2A (3.36 g, 18.02 mmol) in THF (12.50 mL) was added and the mixture was stirred at room temperature for 1 h. The mixture was added slowly to stirring $Et_2O$ (1000 mL), the resultant slurry was filtered. The filter cake was washed with $Et_2O$ (3×100 mL) and vacuum dried to provide Example 2 (11.3166 g, 99% yield) as an off-white, amorphous solid. $^1$H NMR (400 MHz, DMSO-$d_6$) δ 8.59 (d, J=2.7 Hz, 1H), 8.05 (d, J=8.8 Hz, 1H), 7.62 (dd, J=8.2, 2.7 Hz, 1H), 7.58 (s, 1H), 7.37 (s, 1H), 6.81 (t, J=2.5 Hz, 1H), 6.42 (d, J=3.8 Hz, 1H), 4.46 (s, 1H), 4.39-4.19 (m, 4H), 3.54-3.49 (m, 2H), 3.34-3.22 (m, 8H), 2.08-1.93 (m, 1H), 1.74-1.57 (m, 3H), 0.93 (t, J=7.4 Hz, 3H).

Example 3

Potassium Salt of 3-(((1S)-1-(methoxymethyl)propyl)oxy)-5-((6-(methylsulfonyl)-3-pyridinyl)oxy)-N-(4-((2-oxido-1,3,2-dioxaphosphinan-2-yl)methyl)-1,3-thiazol-2-yl)benzamide Example 1 (0.2 g, 0.327 mmol) was dissolved in THF (Ratio: 16.00, Volume: 8 mL) in a 25 mL 1 neck pear shaped flask that was equipped with a magnetic stirrer and an argon inlet. A solution of potassium 4-pentylphenolate (0.066 g, 0.327 mmol) in THF (Ratio: 1.000, Volume: 0.5 mL) was added and the mixture was stirred at room temperature for 2 h. The mixture was added dropwise to stirring $Et_2O$ (100 mL). The resultant slurry was filtered, the filter cake was washed with Et$_2$O (3×1 mL) and vacuum dried to provide Example 3 (0.1927 g, 91% yield) as a pale yellow, amorphous solid. 1H NMR (400 MHz, DMSO-d$_6$) δ ppm 8.60 (1H, d, J=2.75 Hz), 8.05 (1H, d, J=8.79 Hz), 7.63 (1H, dd, J=8.79, 2.75 Hz), 7.57 (1H, s), 7.37 (1H, s), 6.83 (1H, br. s.), 6.46 (1H, br. s.), 4.43-4.52 (1H, m), 4.21-4.38 (4H, m), 3.52 (2H, d, J=5.50 Hz), 3.21-3.34 (8H, m), 1.92-2.07 (1H, m), 1.59-1.73 (3H, m), 0.93 (3H, t, J=7.42 Hz).

Example 4

Crystal Forms of 3-(((1S)-1-(methoxymethyl)propyl)oxy)-5-((6-(methylsulfonyl)-3-pyridinyl)oxy)-N-(4-((2-oxido-1,3,2-dioxaphosphinan-2-yl)methyl)-1,3-thiazol-2-yl)benzamide Crystal forms of 3-(((1S)-1-(methoxymethyl)propyl)oxy)-5-((6-(methylsulfonyl)-3-pyridinyl)oxy)-N-(4-((2-oxido-1,3,2-dioxaphosphinan-2-yl)methyl)-1,3-thiazol-2-yl)benzamide, free base were prepared and characterized as described below.

Procedures for Characterizing the Forms

Single Crystal Data

Data were collected on a Bruker-Nonius (BRUKER AXS, Inc., 5465 East Cheryl Parkway Madison, Wis. 53711 USA) CAD4 serial diffractometer. Unit cell parameters were obtained through least-squares analysis of the experimental diffractometer settings of 25 high-angle reflections. Intensities were measured using Cu Kα radiation (λ=1.5418 Å) at a constant temperature with the θ-2θ variable scan technique and were corrected only for Lorentz-polarization factors. Background counts were collected at the extremes of the scan for half of the time of the scan. Alternately, single crystal data were collected on a Bruker-Nonius Kappa CCD 2000 system using Cu Kα radiation (λ=1.5418 Å). Indexing and processing of the measured intensity data were carried out with the HKL2000 software package (Otwinowski, Z. et al. in *Macromolecular Crystallography*, Vol. 276, pp. 307-326, Carter, W. C., Jr. et al., eds., Academic, NY (1997)) in the Collect program suite. (Collect Data collection and processing user interface: Collect: Data collection software, R. Hooft, Nonius B. V., 1998.) Alternately, single crystal data were collected on a Bruker-AXS APEX2 CCD system using Cu Kα radiation (λ=1.5418 Å). Indexing and processing of the measured intensity data were carried out with the APEX2 software package/program suite (APEX2 Data collection and processing user interface: APEX2 User Manual, v1.27; BRUKER AXS, Inc., 5465 East Cheryl Parkway Madison, Wis. 53711 USA).

When indicated, crystals were cooled in the cold stream of an Oxford cryo system (Oxford Cryosystems Cryostream cooler: Cosier, J. et al., *J. Appl. Cryst.*, 19:105 (1986)) during data collection.

The structures were solved by direct methods and refined on the basis of observed reflections using either the SDP (SDP, Structure Determination Package, Enraf-Nonius, Bohemia N.Y. 11716. Scattering factors, including f' and f", in the SDP software were taken from the "International Tables for Crystallography", Vol. IV, Tables 2.2A and 2.3.1, Kynoch Press, Birmingham, England (1974)) software package with minor local modifications or the crystallographic packages MAXUS (maXus solution and refinement software suite: Mackay, S. et al., maXus: a computer program for the solution and refinement of crystal structures from diffraction data or SHELXTL[4]. The derived atomic parameters (coordinates and temperature factors) were refined through full matrix least-squares. The function minimized in the refinements was $\Sigma_w(|F_o|-|F_c|)^2$. R is defined as $\Sigma||F_o|-|F_c||/\Sigma|F_o|$ while $R_w=[\Sigma_w(|F_o|-|F_c|)^2/\Sigma_w|F_o|^2]^{1/2}$ where w is an appropriate weighting function based on errors in the observed intensities. Difference maps were examined at all stages of refinement. Hydrogens were introduced in idealized positions with isotropic temperature factors, but no hydrogen parameters were varied.

X-ray Powder Diffraction Data (PXRD)

PXRD data were obtained using a Bruker C2 GADDS. The radiation was Cu Kα (40 KV, 40 mA). The sample-detector distance was 15 cm. Powder samples were placed in sealed glass capillaries of 1 mm or less in diameter; the capillary was rotated during data collection. Data were collected for 3≤2θ≤35° with a sample exposure time of at least 1000 seconds. The resulting two-dimensional diffraction arcs were integrated to create a traditional 1-dimensional PXRD pattern with a step size of 0.02 degrees 2θ in the range of 3 to 35 degrees 2θ.

Differential Scanning Calorimetry (DSC)

DSC experiments were performed in a TA INSTRUMENTS® model Q1000 or 2920. The sample (about 2-6 mg) was weighed in an aluminum pan and recorded accurately recorded to a hundredth of a milligram, and transferred to the DSC. The instrument was purged with nitrogen gas at 50 mL/min. Data were collected between room temperature and 300° C. at 10° C./min heating rate. The plot was made with the endothermic peaks pointing down.

Thermal Gravimetric Analysis (TGA)

TGA experiments were performed in a TA INSTRUMENTS® model Q500 or 2950. The sample (about 10-30 mg) was placed in a platinum pan previously tared. The weight of the sample was measured accurately and recorded to a thousandth of a milligram by the instrument. The furnace was purged with nitrogen gas at 100 mL/min. Data were collected between room temperature and 300° C. at 10° C./min heating rate.

Preparation and Analysis of the Forms

Form Preparation, PXRD, DSC and TGA Characterization

Example 4a, Form N-1: Crude Example 1 (20.77 g) was recrystallized twice from absolute ethanol (175 mL each time) to provide the N-1 form material (16.0 g; 73%) as a white crystalline solid. Crystals were grown from Example 1 as colorless needles in absolute ethanol solution. Form N-1 was characterized by a DSC thermogram having an endothermic onset typically ca. 166° C., at higher temperatures other events may ensue. Form N-1 was characterized by a PXRD pattern which matches the simulated pattern generated from the single crystal structure data. Form N-1 was also characterized by a TGA curve having negligible weight loss at up to ca. 275° C. and in agreement with the single-crystal structure.

Example 4a is characterized by unit cell parameters substantially equal to the following:

Cell dimensions:
  a=8.0531 (2)
  b=13.5078 (3)
  c=13.7063 (3)
  α=73.091 (1)
  β=88.186 (1)
  γ=89.881 (1)
  Space group: P1

Molecules/asymmetric unit (Z'): 2
Density, calc g·cm$^{-3}$: 1.425.

Alternatively, Example 4a was prepared as follows:

Dichloromethane (28 L, 11 vol) followed by crude Example 1 (2.53 kg, 1.0 eq) were added to a 30 L reactor at ambient temperature. The resulting mixture was stirred for 10 minutes to affect dissolution and then aluminum oxide (2.82 kg, 6.7 eq) was added. Upon completion of addition, the reaction mixture was stirred for 30 minutes. After this time, the reaction mixture was filtered through a 3 kg celite bed and then the celite bed was washed with dichloromethane (30.4 L, 12 vol). The combined filtrates were concentrated in vacuo and then polish filtered ethanol (6 L) was added. Upon completion of addition, the resulting mixture was concentrated under reduced temperature (below 55° C.) to provide a concentrated mixture (7 L, 3 Vol). Polish filtered ethanol (30 L, 12 vol) was added to the concentrated mixture and the resulting mixture was heated to 60° C. to 65° C. Once at the prescribed temperature, seed crystals of Example 4a (12.5 g) were added and then the reaction mixture was stirred at 60 to 65° C. for 30 min. At the conclusion of this period, the reaction mixture was cooled to 25° C. where it stirred for 4 h. After this time, the reaction mixture was filtered in a centrifuge, washed with ethanol (5 L) and then spun dried for 1 hour. At the conclusion of this period, the resulting material was dried in in vacuo at 65° C. for 6 hours to provide Example 4a (2.27 kg).

Example 4a was also prepared as follows:

Crude Example 1 (50 mg) was dissolved in absolute EtOH (15 vol-eq) at 75° C. Upon completion of dissolution, the solution was cooled to 20° C. where it was maintained for a period of no less than one hour and no more than 4 h to provide Example 4a as a white crystalline solid.

Crude Example 1 (50 mg) was dissolved in n-butanol (15 vol-eq) at 90° C. Upon completion of dissolution, the solution was cooled to 20° C. where it was maintained for a period of no less than one hour and no more than 4 h to provide Example 4a as a white crystalline solid.

Crude Example 1 (50 mg) was dissolved in iso-butanol (15 vol-eq) at 80° C. Upon completion of dissolution, the solution was cooled to 20° C. where it was maintained for a period of no less than one hour and no more than 4 h to provide Example 4a as a white crystalline solid.

Crude Example 1 (50 mg) was dissolved in tert-butanol (15 vol-eq) at 80° C. Upon completion of dissolution, the solution was cooled to 30° C. where it was maintained for a period of no less than one hour and no more than 4 h to provide Example 4a as a white crystalline solid.

Crude Example 1 (50 mg) was dissolved in dimethyl sulfoxide (4 vol-eq) at 20° C. Upon completion of dissolution, water (9.5 vol-eq) was added over a period of no less than 30 min and no more than 1 hour. Upon completion of addition, the resulting mixture was stirred at 20° C. for no less than 12 hours to provide Example 4a as a white crystalline solid.

Crude Example 1 (50 mg) was dissolved in dimethyl formamide (4 vol-eq) at 20° C. Upon completion of dissolution, water (20 vol-eq) was added over a period of no less than 30 min and no more than 1 hour. Upon completion of addition, the resulting mixture was stirred at 20° C. for no less than 12 hours to provide Example 4a as a white crystalline solid.

Crude Example 1 (50 mg) was dissolved in acetone (30 vol-eq) at 50° C. Upon completion of dissolution, water (15 vol-eq) was added over a period of no less than 30 min and no more than 1 hour. Upon completion of addition, the resulting mixture was concentrated to no less than 20 vol-eq and no more than 30 vol-eq. Once at the prescribed concentration, the heat was removed and the mixture was allowed to cool to 20° C. for no less than 12 hours to provide Example 4a as a white crystalline solid.

Example 4b, Fumaric Acid Cocrystal, Form P-2: Example 4a was dissolved in MeOH (20 L/kg) at 20° C. and then the solvent was removed by distillation under vacuum over night to yield a residue. To the resulting residue was added a mixture of ethyl acetate and heptanes (20 L/kg, a ratio of 1:2 v:v) to obtain a slurry. The resulting slurry was heated to 50° C. where it stirred vigorously for 2 h. After this time, the slurry was cooled to 25° C. where it stirred for 3 h. At the conclusion of this period, the resulting solids were isolated by centrifugation to provide Example 4b as a (1:1) fumaric acid salt. $^1$H NMR (400 MHz, CHLOROFORM-d) δ 8.36 (d, J=2.7 Hz, 1H), 7.92 (d, J=8.8 Hz, 1H), 7.54 (s, 1H), 7.37 (dd, J=8.8, 2.7 Hz, 1H), 7.34 (s, 1H), 6.77 (t, J=2.2 Hz, 1H), 6.72 (d, J=3.8 Hz, 1H), 6.64 (s, 2H), 4.45-4.36 (m, 1H), 4.36-4.25 (m, 2H), 4.13-3.99 (m, 2H), 3.49-3.40 (m, 2H), 3.32-3.19 (m, 5H), 3.09 (s, 3H), 1.87 (s, 2H), 1.75-1.56 (m, 4H), 0.86 (t, J=7.4 Hz, 3H). Form P-2 was characterized by a PXRD pattern.

Examples 5 and 6

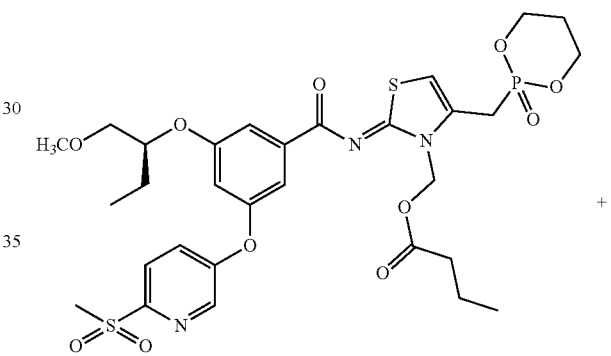

Example 5

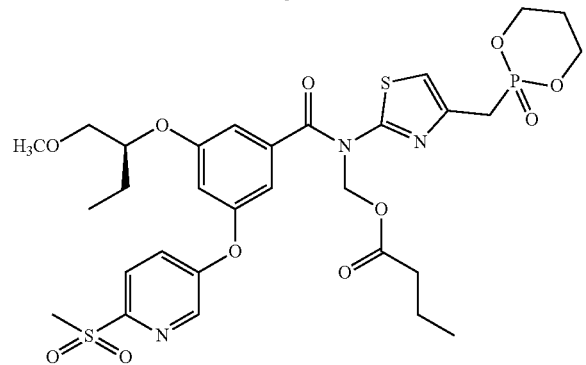

Example 6

Intermediate 5A—Iodomethyl butyrate

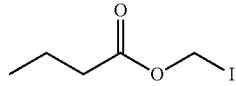

To a solution of chloromethyl butyrate (0.25 g, 1.83 mmol) in acetone (50 mL) in a 100 mL 1 neck round-bottom flask (under argon and protected from light by aluminum foil) was added NaI (0.549 g, 3.66 mmol). The reaction mixture was stirred at room temperature overnight, then was filtered; the filter cake was washed with acetone (5 mL) and the combined filtrates were concentrated in vacuo to provide an orange oil which was triturated with $Et_2O$ (10 mL) and filtered. The remaining material was concentrated in vacuo to provide Intermediate 5A (0.291 g, 70% yield) as a brown oil, which was used in the next reaction without further purification.

Examples 5 and 6

To a solution of Example 1 (0.2 g, 0.327 mmol) in DMF (5 mL) under Argon were successively added $Cs_2CO_3$ (0.266 g, 0.817 mmol; dried in vacuo with heating) and N,O-bis(trimethylsilyl)acetamide (0.333 g, 1.64 mmol), followed by dropwise addition of a solution of Intermediate 5A (0.112 g, 0.490 mmol) in DMF (1 mL). The reaction mixture was stirred at room temperature for 30 min, after which the reaction was determined to be complete by analytical HPLC and LC/MS. The reaction mixture was then poured into water (15 mL) and extracted with EtOAc (2×15 mL); the combined organic extracts were dried ($MgSO_4$) and concentrated in vacuo to provide a yellow oil. This material was dissolved in $CH_3CN$ (2 mL) and purified by preparative HPLC [Luna—5μ C-18(2) 100A—30×250 mm column, detection at 220 nm; flow rate=40 mL/min; continuous gradient from 0% B to 100% B over 25 min+5 min hold time at 100% B, where A=90:10 $H_2O$:MeCN and B=10:90 $H_2O$:MeCN]. The faster eluting product 1 (retention time 19.1 min) was concentrated in vacuo to provide a white solid. The slower eluting product 2 (retention time 19.6 min) was also concentrated in vacuo to provide a white solid. The faster eluting product 1 (impure) was dissolved in $CH_3CN$ (2 mL) and further purified by preparative HPLC [Luna—5μ C-18(2) 100A—30×250 mm column, detection at 220 nm; flow rate=40 mL/min; continuous gradient from 0% B to 100% B over 25 min+5 min hold time at 100% B, where A=90:10 $H_2O$:MeCN:$CF_3CO_2H$ and B=10:90 $H_2O$:MeCN:$CF_3CO_2H$] to provide Example 6 (19 mg; 8% yield) as a white solid. Analytical HPLC [Luna—5μ C-18(2) 100A—2.0×50 mm column, detection at 220 nm; flow rate=0.8 mL/min; continuous gradient from 0% B to 100% B over 4 min+1 min hold time at 100% B where A=90:10:0.1 $H_2O$:MeCN:$CF_3CO_2H$ and B=10:90:0.1 $H_2O$:MeCN:$CF_3CO_2H$] Retention time=3.60 min, 100% purity; $[M+H]^+$=712.2; $^1$H NMR (400 MHz, $CDCl_3$) δ 8.49 (d, J=2.2 Hz, 1H), 8.07 (d, J=8.2 Hz, 1H), 7.50 (dd, J=8.5, 2.5 Hz, 1H), 7.08 (s, 1H), 7.06 (d, J=3.8 Hz, 1H), 6.89 (s, 1H), 6.86 (s, 1H), 6.07 (s, 2H), 4.55-4.42 (m, 2H), 4.40-4.24 (m, 4H), 3.59-3.52 (m, 2H), 3.41 (d, J=20.3 Hz, 3H), 3.36 (s, 3H), 3.23 (s, 3H), 2.29 (t, J=7.4 Hz, 2H), 2.19-2.07 (m, 1H), 1.95-1.83 (m, 1H), 1.78-1.68 (m, 2H), 1.67-1.56 (m, 2H), 0.98 (t, J=7.4 Hz, 3H), 0.93 (t, J=7.4 Hz, 3H).

The slower eluting fraction 2 (impure) was dissolved in $CH_3CN$ (2 mL) and the material was further purified by preparative HPLC [Luna—5μ C-18(2) 100A—30×250 mm column, detection at 220 nm; flow rate=40 mL/min; continuous gradient from 40% B to 70% B over 30 min+5 min hold time at 100% B where A=90:10 $H_2O$:MeCN and B=10:90 $H_2O$:MeCN] to provide Example 5 (119 mg, 50% yield) as a white solid. Analytical HPLC [Luna—5μ C-18(2) 100A—2.0×50 mm column, detection at 220 nm; flow rate=0.8 mL/min; continuous gradient from 0% B to 100% B over 4 min+1 min hold time at 100% B where A=90:10: 0.1 $H_2O$:MeCN:$CF_3CO_2H$ and B=10:90:0.1 $H_2O$:MeCN:$CF_3CO_2H$] Retention time=3.70 min, 98.8% purity; $[M+H]^+$=712.2; $^1$H NMR (400 MHz, $CDCl_3$): δ 8.50 (d, J=2.7 Hz, 1H), 8.04 (d, J=8.2 Hz, 1H), 7.86-7.83 (m, 1H), 7.63-7.60 (m, 1H), 7.45 (dd, J=8.2, 2.7 Hz, 1H), 6.88-6.84 (m, 1H), 6.60 (d, J=4.9 Hz, 1H), 6.37 (s, 2H), 4.64-4.54 (m, 2H), 4.53-4.45 (m, 1H), 4.37-4.25 (m, 2H), 3.63-3.59 (m, 2H), 3.51 (d, J=20.9 Hz, 2H), 3.39 (s, 3H), 3.22 (s, 3H), 2.30 (t, J=7.4 Hz, 2H), 2.15-1.97 (m, 2H), 1.83-1.73 (m, 2H), 1.66-1.55 (m, 2H), 1.01 (t, J=7.4 Hz, 3H), 0.89 (t, J=7.4 Hz, 3H).

Alternatively, Example 6 can prepared according to the following procedure:

Intermediate 6A

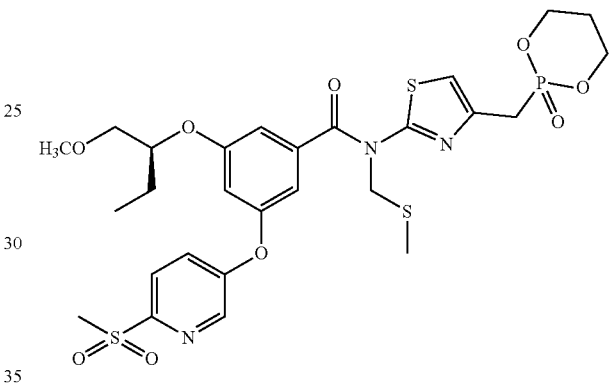

To a solution of Example 1 (1.5 g, 2.452 mmol) in $CH_2Cl_2$ (15 mL) in a 48 mL glass sealed tube equipped with a magnetic stirrer were successively added phosphazene base P1-t-Bu-tris(tetramethylene) (1.532 g, 4.90 mmol) and (chloromethyl)(methyl)sulfane (0.284 g, 2.94 mmol). The reaction tube was flushed with Ar, capped and the reaction mixture was stirred at 50° C. overnight, and then was cooled to room temperature. The reaction mixture was concentrated in vacuo to provide a brown oil, which was dissolved in a minimal amount of $CH_2Cl_2$ and chromatographed (120 g $SiO_2$; gradient from 0-100% EtOAC in hexane over 35 min, followed by 0-10% MeOH in $CH_2Cl_2$ over 35 min) to provide Intermediate 6A (1.029 g, 62% yield) as a yellow foam. Analytical HPLC [Luna—5μ C-18(2) 100A—2.0×50 mm column, detection at 220 nm; flow rate=0.8 mL/min; continuous gradient from 0% B to 100% B over 4 min+1 min hold time at 100% B where A=90:10:0.1 $H_2O$:MeCN:$CF_3CO_2H$ and B=10:90:0.1 $H_2O$:MeCN:$CF_3CO_2H$] Retention time=3.403 min., $[M+H]^+$=671.9, $^1$H NMR (400 MHz, $CDCl_3$): δ 8.48 (d, J=2.7 Hz, 1H), 8.07 (d, J=8.8 Hz, 1H), 7.48 (dd, J=8.2, 2.7 Hz, 1H), 7.04-6.99 (m, 2H), 6.85-6.82 (m, 1H), 6.81 (s, 1H), 5.27 (s, 2H), 4.57-4.43 (m, 3H), 4.41-4.32 (m, 1H), 4.31-4.19 (m, 3H), 3.60-3.52 (m, 3H), 3.43 (d, J=20.9 Hz, 2H), 3.38 (s, 3H), 3.23 (s, 4H), 2.22 (s, 3H), 2.10-1.98 (m, 2H), 1.97-1.85 (m, 1H), 1.78-1.68 (m, 3H), 0.98 (t, J=7.4 Hz, 4H).

Intermediate 6B

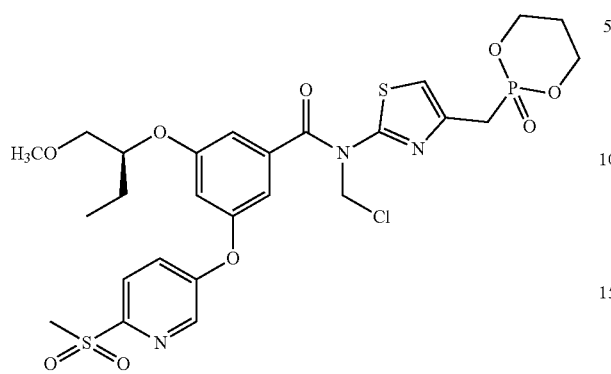

To a solution of Intermediate 6A (0.400 g, 0.595 mmol) in CH$_2$Cl$_2$ (12.5 mL) under Ar was added triethylamine hydrochloride (0.246 g, 1.79 mmol), followed by dropwise addition of sulfuryl chloride (0.595 mL, 0.595 mmol). The reaction mixture was stirred at room temperature under Ar for 90 min, after which the reaction was complete by analytical HPLC and LC/MS. The reaction mixture was concentrated in vacuo to provide Intermediate 6B (393 mg; 0.595 mmol; 100% crude yield) as a white solid that was used in the next reaction without further purification. Analytical HPLC [Luna—5μ C-18(2) 100A—2.0×50 mm column, detection at 220 nm; flow rate=0.8 mL/min; continuous gradient from 0% B to 100% B over 4 min+1 min hold time at 100% B where A=90:10:0.1 H$_2$O:MeCN:CF$_3$CO$_2$H and B=10:90:0.1 H$_2$O:MeCN:CF$_3$CO$_2$H]; Retention time=3.335 min., [M+H]$^+$=656 (methanol adduct).

Example 6

To a solution of Intermediate 6B (0.393 g, 0.595 mmol) in MeCN (10 mL) under Ar were successively added butyric acid (0.163 mL, 1.79 mmol) and K$_2$CO$_3$ (0.329 g, 2.38 mmol). The reaction mixture was stirred at 60° C. for 3 h, after which analytical HPLC and LC/MS indicated that the reaction was complete. The reaction mixture was cooled to room temperature and filtered; the remaining solids were washed with MeCN (2 mL) and the combined filtrates were concentrated in vacuo to ~2 mL in volume. This crude material was purified twice by preparative HPLC [Phen Luna AXIA –5μ C-18-30×100 mm column, detection at 220 nm; flow rate=40 mL/min; continuous gradient from 10% B to 75% B over 20 min+2 min hold time at 100% B where A=90:10 H$_2$O:MeCN and B=10:90 H$_2$O:MeCN] to provide Example 6 (277 mg, 64% yield) as a white solid. Analytical HPLC (Sunfire C18 3.5 μM, 3.0×150 mm column, detection at 220 and 254 nm; flow rate=1 mL/min; continuous gradient from 10% B to 100% B over 12 min+3 min hold time at 100% B where A=95:5:0.05 H$_2$O:MeCN:CF$_3$CO$_2$H and B=5:95:0.05 H$_2$O:MeCN:CF$_3$CO$_2$H); Retention time=9.62 min; purity=98%; [M+H]$^+$=712.0, $^1$H NMR (400 MHz, CDCl$_3$) δ 8.49 (d, J=2.2 Hz, 1H), 8.07 (d, J=8.2 Hz, 1H), 7.50 (dd, J=8.5, 2.5 Hz, 1H), 7.08 (s, 1H), 7.06 (d, J=3.8 Hz, 1H), 6.89 (s, 1H), 6.86 (s, 1H), 6.07 (s, 2H), 4.55-4.42 (m, 2H), 4.40-4.24 (m, 4H), 3.59-3.52 (m, 2H), 3.41 (d, J=20.3 Hz, 3H), 3.36 (s, 3H), 3.23 (s, 3H), 2.29 (t, J=7.4 Hz, 2H), 2.19-2.07 (m, 1H), 1.95-1.83 (m, 1H), 1.78-1.68 (m, 2H), 1.67-1.56 (m, 2H), 0.98 (t, J=7.4 Hz, 3H), 0.93 (t, J=7.4 Hz, 3H).

Example 7

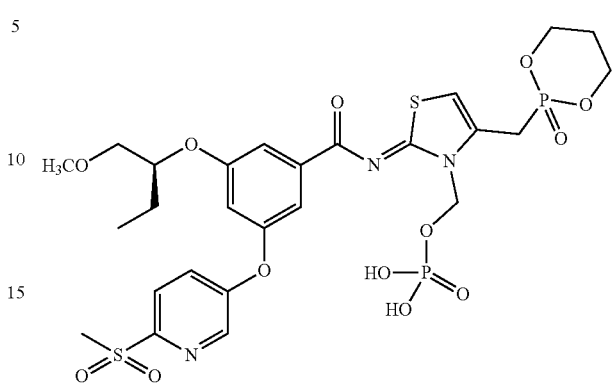

Intermediate 7A

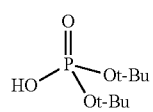

Concentrated HCl (2.89 mL, 34.6 mmol) was added slowly to a solution of potassium di-tert-butyl phosphate (8.6 g, 34.6 mmol) in water (10 mL) at 0° C. The precipitated solid was collected by filtration, washed with a small amount of ice-water (~5 mL), and dried in vacuo to provide Intermediate 7A (7.1 g, 33.8 mmol, 98% yield) as a white solid.

Intermediate 7B

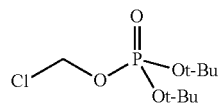

A mixture of Intermediate 7A (2.9 g, 13.8 mmol), Bu$_4$NHSO$_4$ (0.468 g, 1.38 mmol) and NaHCO$_3$ (9.27 g, 110 mmol) in water and CH$_2$Cl$_2$ (50 mL each) was stirred at 0° C. for 10 min, followed by dropwise addition of chloromethyl chlorosulfate (2.09 mL, 20.7 mmol) over 30 min. The reaction was then stirred at room temperature for 18 h, after which the organic layer was washed with brine, dried (MgSO$_4$) and concentrated in vacuo. The residue was chromatographed (24 g SiO$_2$; continuous gradient of EtOAc/Hexane (0% to 30% over 15 min) to provide Intermediate 7B (2.1 g, 8.12 mmol, 59% yield) as a clear oil. $^1$H NMR (400 MHz, CDCl$_3$) δ 5.63 (d, J=14.8 Hz, 2H), 1.54-1.49 (s, 18H); $^{31}$P NMR (162 MHz, CDCl$_3$) δ –11.94 (s).

Intermediate 7C

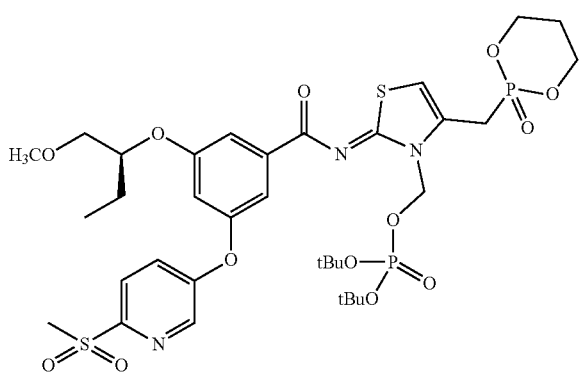 [SMILES: CC[C@@H](COC)Oc1cc(Oc2ccc(S(C)(=O)=O)nc2)cc(C(=O)/N=c2\scc(CP3(=O)OCCCO3)n2COP(=O)(OC(C)(C)C)OC(C)(C)C)c1]

To a solution of Example 1 (250 mg, 0.409 mmol) in DMF (7.5 mL) under Ar were successively added Intermediate 7B (254 mg, 0.981 mmol), Bu$_4$NI (53 mg, 0.143 mmol) and Cs$_2$CO$_3$ (333 mg, 1.02 mmol), and the reaction mixture was stirred overnight at 35° C., after which the reaction was complete by analytical HPLC and LC/MS. The reaction was cooled to room temperature, filtered, and the remaining solids were washed with CH$_2$Cl$_2$ (25 mL). The combined filtrates were concentrated in vacuo to provide a yellow oil that was dissolved in MeOH (2 mL) and purified by preparative HPLC [Luna—5μ C-18(2) 30×250 mm column, detection at 220 nm; flow rate=20 mL/min; continuous gradient from 40% B to 100% B over 30 min+7 min hold time at 100% B where A=90:10:0.1 H$_2$O:MeOH:CF$_3$CO$_2$H and B=10:90:0.1 H$_2$O: MeOH:CF$_3$CO$_2$H] to provide Intermediate 7C (0.1768 g, 51.9% yield) as a clear oil. Analytical HPLC [Luna—5μ C-18(2) 100A—2.0×50 mm column, detection at 220 nm; flow rate=0.8 mL/min; continuous gradient from 0% B to 100% B over 4 min+1 min hold time at 100% B where A=90:10:0.1 H$_2$O:MeCN:CF$_3$CO$_2$H and B=10:90:0.1 H$_2$O:MeCN:CF$_3$CO$_2$H]; Retention time=3.78 min., [M+H]$^+$=834.3, $^1$H NMR (400 MHz, CDCl$_3$) δ 8.47 (d, J=2.7 Hz, 1H), 8.03 (d, J=8.2 Hz, 1H), 7.86-7.83 (m, 1H), 7.67-7.64 (m, 1H), 7.42 (dd, J=8.8, 2.8 Hz, 1H), 6.86-6.82 (m, 1H), 6.63 (d, J=4.4 Hz, 1H), 6.23 (d, J=10.4 Hz, 2H), 4.62-4.51 (m, 2H), 4.50-4.42 (m, 1H), 4.39-4.28 (m, 2H), 3.65-3.54 (m, 4H), 3.38 (s, 3H), 3.22 (s, 3H), 2.11-2.03 (m, 1H), 1.79-1.71 (m, 2H), 1.58-1.52 (m, 1H), 1.42 (s, 18H), 1.00 (t, J=7.4 Hz, 3H).

Example 7

A solution of Intermediate 7C (177 mg, 0.212 mmol) in AcOH:water (6.25 mL of a 4:1 mixture) was stirred at 60° C. under Ar for 2 h, after which analytical HPLC and LC/MS indicated that the reaction was complete. Volatiles were removed in vacuo to provide a clear oil, which was dissolved in MeOH (4 mL) and purified twice by preparative HPLC [XBridge Prep Phenyl −5μ OBD—19×100 mm column, detection at 220 nm; flow rate=20 mL/min; continuous gradient from 0% B to 75% B over 20 min+5 min hold time at 100% B where A=90:10:0.1 H$_2$O:MeOH:CF$_3$CO$_2$H and B=10:90:0.1 H$_2$O: MeOH:CF$_3$CO$_2$H] to provide Example 7 (77 mg, 48% yield) as a white solid. Analytical HPLC [Luna—5μ C-18(2) 100A—2.0×50 mm column, detection at 220 nm; flow rate=0.8 mL/min; continuous gradient from 0% B to 100% B over 4 min+1 min hold time at 100% B where A=90:10:0.1 H$_2$O:MeCN:CF$_3$CO$_2$H and B=10:90:0.1 H$_2$O:MeCN:CF$_3$CO$_2$H]; Retention time=3.02 min, 99.7% purity; [M+H]$^+$=722.0, $^1$H NMR (400 MHz, CDCl$_3$) δ 8.45 (d, J=2.7 Hz, 1H), 8.01 (d, J=8.2 Hz, 1H), 7.66 (s, 1H), 7.56 (s, 1H), 7.50 (dd, J=8.8, 2.7 Hz, 1H), 6.92 (d, J=3.8 Hz, 1H), 6.89 (t, J=2.2 Hz, 1H), 6.13 (d, J=11.0 Hz, 2H), 4.51-4.30 (m, 5H), 3.64-3.54 (m, 4H), 3.37 (s, 3H), 3.17 (s, 3H), 2.11-1.99 (m, 1H), 1.98-1.87 (m, 1H), 1.79-1.65 (m, 2H), 0.97 (t, J=7.4 Hz, 3H), $^{31}$P NMR (162 MHz, CDCl$_3$) δ 17.4 (s), −0.65 (s).

Examples 8 and 9

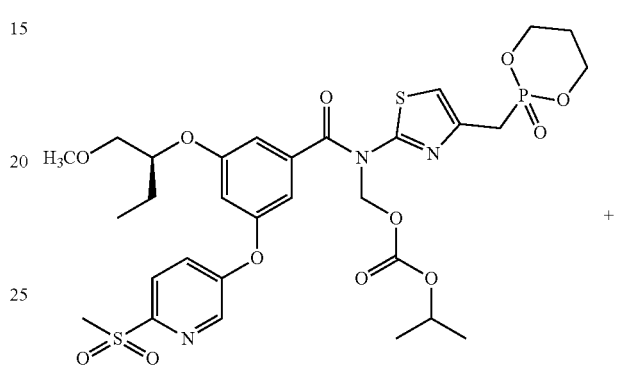

Example 8

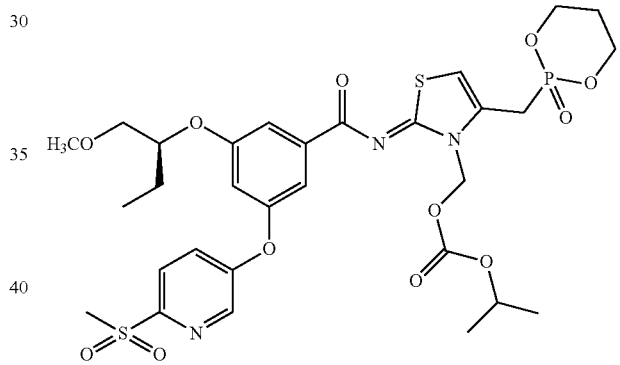

Example 9

To a stirred solution of Example 1 (100 mg, 0.163 mmol) in MeCN (5 mL) at RT was added N,O-bis(trimethylsilyl)acetamide (162 μL, 0.654 mmol). After 5 min, K$_2$CO$_3$ (45 mg, 0.33 mmol) was added, followed by chloromethyl isopropyl carbonate (49.9 mg, 0.327 mmol). The reaction was stirred at RT for 30 min, then heated at 45° C. for 16 h, after which it was cooled to RT. The reaction mixture was concentrated in vacuo and EtOAc was added. The organic layer was washed with saturated aqueous NH$_4$Cl, dried over MgSO$_4$, filtered and concentrated in vacuo. The crude material was purified by preparative HPLC (Phenomenex Luna AXIA 5 μm C18 30×100 mm column; detection at 220 nm; flow rate=10 mL/min; continuous gradient from 0% B to 100% B over 30 min+7 min hold time at 100% B, where A=90:10 H$_2$O:MeOH and B=90:10 MeOH:H$_2$O) to provide slightly impure Example 8 and Example 9. Examples 8 and 9 were each further purified by chromatography (4 g SiO$_2$ column; continuous gradient from 0%-12% MeOH in EtOAc) to provide highly purified Example 8 (14 mg, 0.019 mmol, 12% yield) and Example 9 (34 mg, 0.047 mmol, 29% yield) as white solids.

Example 8

Analytical HPLC (Sunfire C18 3.5 μM, 3.0×150 mm column, detection at 220 and 254 nm; flow rate=1 mL/min; continuous gradient from 10% B to 100% B over 15 min+3 min hold time at 100% B where A=95:5:0.05 $H_2O$:MeCN:$CF_3CO_2H$ and B=5:95:0.05 $H_2O$:MeCN:$CF_3CO_2H$); Retention time=9.17 min; purity=97%; $[M+H]^+$=728.3. $^1H$ NMR (500 MHz, $CDCl_3$) δ: 8.50 (d, J=2.20 Hz, 1H), 8.08 (d, J=8.25 Hz, 1H), 7.50 (dd, J=2.75, 8.80 Hz, 1H), 7.09 (m, 1H), 7.04 (d, J=3.85 Hz, 1H), 6.90 (m, 1H), 6.87 (m, 1H), 6.10 (s, 2H), 4.86 (m, 1H), 4.43-4.50 (m, 2H), 4.37 (m, 1H), 4.22-4.31 (m, 2H), 3.57 (m, 2H), 3.44 (d, J=20.63 Hz, 2H), 3.37 (s, 3H), 3.24 (s, 3H), 2.09 (m, 1H), 1.84 (m, 1H), 1.74 (M, 2H), 1.29 (d, J=6.33 Hz, 6H), 0.99 (t, J=7.43 Hz, 3H). $^{31}P$ NMR (202.45 MHz, $CDCl_3$) δ: 18.66.

Example 9

Analytical HPLC (Sunfire C18 3.5 μM, 3.0×150 mm column, detection at 220 and 254 nm; flow rate=1 mL/min; continuous gradient from 10% B to 100% B over 15 min+3 min hold time at 100% B where A=95:5:0.05 $H_2O$:MeCN:$CF_3CO_2H$ and B=5:95:0.05 $H_2O$:MeCN:$CF_3CO_2H$); Retention time=9.35 min; Analytical purity=98.5%; $[M+H]^+$=728.3. $^1H$ NMR (500 MHz, $CDCl_3$) δ: 8.47 (d, J=2.20 Hz, 1H), 8.00 (d, J=8.79 Hz, 1H), 7.82 (s, 1H), 7.60 (s, 1H), 7.42 (dd, J=2.75, 8.79 Hz, 1H), 6.82 (m, 1H), 6.56 (d, J=4.40 Hz, 1H), 6.39 (s, 2H), 4.80-4.86 (m, 1H), 4.49-4.58 (m, 2H), 4.46 (m, 1H), 4.24-4.33 (m, 2H), 3.57 (m, 2H), 3.50 (d, J=20.34 Hz, 2H), 3.36 (s, 3H), 3.19 (s, 3H), 2.01 (m, 1H), 1.74 (m, 2H), 1.74 (M, 2H), 1.24 (d, J=6.05 Hz, 6H), 0.97 (t, J=7.15 Hz, 3H).

Assays for Glucokinase Activation

The compound, enantiomer, prodrug, diastereomer, or salt thereof, of the present invention activates glucokinase. Assays which may be used in testing the compound, enantiomer, prodrug, diastereomer, or salt thereof, of the present invention in activating glucokinase are known in the art such as disclosed in U.S. Pat. Nos. 6,320,050, 6,384,200 and 6,610,846 and WO 004/052869 and in Castellano, A. L. et al., "Glucokinase activating ureas", *Bioorg. Med. Chem. Letters,* 15:1501-1504 (2005), and Grimsby, J., et al., "Allosteric Activators of Glucokinase: Potential Role in Diabetes Therapy", *Science,* 301:370-373 (2003).

In general, the compound, enantiomer, prodrug, diastereomer, or salt thereof, of the present invention has been identified to enhance the activity of glucokinase at concentrations equivalent to, or more potently than, 100 μM, preferably 10 μM, more preferably 1 μM, thereby demonstrating that the compound of the present invention is an especially effective enhancer of the activity of glucokinase. Potencies can be calculated and expressed as either $EC_{50}$ (concentration to achieve 50% of full activation) and/or the maximum percentage activation above background, and refer to activity measured employing the assay system described above.

Assay and Biological Data

The compound, enantiomer, prodrug, diastereomer, or salt thereof, of the present invention has been tested in the following assay and has shown to be an activator of glucokinase.

Glucokinase Tandem Enzymatic Assay

Enzymatic activity of human glucokinase (GK) was measured by incubating GK, ATP, and glucose for discrete time periods followed by quenching with EDTA (ethylenediamine tetra-acetic acid). Relative amounts of product glucose-6-phosphate (G6P) were measured by then running a detection assay using G6P dehydrogenase and measuring the conversion of ThioNAD (thio-nicotinamide adenine dinucleotide) to ThioNADH (thio-dihydronicotinamide adenine dinucleotide) at a wavelength of 405 nm. This "uncoupled" enzymatic reaction is denoted as the GK "tandem" assay. Activation of GK by the compound can be assessed using this assay. The GK tandem assay protocol described below was followed using a range of activator compound concentrations from 0 to 100 μM at 5 and 12 mM of glucose. Human full-length glucokinase (GK, 15 nM) was incubated with 5 or 12 mM glucose in a 384 well black microtiter plate with a clear bottom. To initiate the GK reaction, magnesium-ATP (3 mM final concentration) was added to GK in buffer (final buffer conditions of 25 mM HEPES buffer, pH 7.1, containing 1 mM dithiothreitol and 5% DMSO). The total reaction volume was 20 μL. The reaction was allowed to proceed for ten minutes and was then quenched with 5 μL EDTA; 45 mM final). The components of the detection reaction, ThioNAD and G6PDH (glucose-6-phosphate dehydrogenase) (final concentrations of 650 μM and 3.33 Units, respectively), were then added together in a volume of 25 μL, (to give a total volume of 50 μL). Absorbance measurements were made at 405 nm on a SPECTRAMAX® Plus 384 absorbance plate reader (Molecular Devices). Absorbance was read, background glucose-6-phosphate levels were subtracted, after which activation was calculated as a percentage of control activity. Control activity was determined using GK in the presence of vehicle (DMSO), with background glucose-6-phosphate subtracted. Background glucose-6-phosphate was determined by pre-quenching GK with EDTA prior to reaction initiation with ATP.

Expression and Purification of Human GK

Full-length human hepatic GK (untagged) was expressed in BL21 STAR (DE3)pLysS cells (Invitrogen) at 25° C. as described by Mookhtiar et al. (1). The protein was purified essentially as described by Lange (2) with a slight modification. Briefly, cell pellets were lysed via three rounds of freezing and thawing, centrifuged at 15000 g for clarification, and precipitated with 40-65% $(NH_4)_2SO_4$. The resulting pellet was resuspended in buffer, dialyzed, and applied directly to a Q-SEPHAROSE® (Sigma) column followed by elution with a linear 100-600 mM KCl gradient. GK containing fractions were pooled, dialyzed overnight vs. 25 mM Hepes pH 7.2/1 mM MgCl2/1 mM EDTA/0.1 M KCl/1 mM DTT, then dialyzed again with same buffer with 10% glycerol added.

REFERENCES

1. Mookhtiar, K. A. et al., "Heterologous expression and characterization of rat liver glucokinase regulatory protein", *Diabetes,* 45:1670-1677 (1996).
2. Lange, A. J. et al., "Expression and site-directed mutagenesis of hepatic glucokinase", *Biochem. J.,* 277:159-163 (1991).

Find below in Table 1 data for compared compounds (See WO 2008/005964 A1, U.S. Pat. Nos. 7,432,287 and 7,977,367). The comparative data shows the unexpected significant improvement in 1) aqueous solubility, 2) metabolic stability in human liver microsomes; 3) reduction in cytochrome P450 enzyme inhibition and/or 4) inhibition of human glucokinase of the compound of the present invention.

TABLE 1

| | EX. 37 WO 2008/005964 A1 | EX. 54 WO 2008/005964 A1 | EX. 83 WO 2008/005964 A1 | EX. 137 WO 2008/005964 A1 | EX. 169 WO 2008/005964 A1 | EX. 117 U.S. Pat. No. 7,432,287 | EX. 48 U.S. Pat. No. 7,977,367 | Ex. 1 Instant application |
|---|---|---|---|---|---|---|---|---|
| Human Glucokinase $IC_{50}$ (nM) | 135 | 79 | 170 | 156 | 149 | 134 | 337 | 95 |
| Human Glucokinase $EC_{50}$ (nM) | 38 | 49 | 54 | 21 | 54 | 64 | 348 | 36 |
| Human Glucokinase Ymax (maximal activation) | 204% | 176% | 170% | 169% | 187% | 183% | 255% | 194% |
| Mouse Glucokinase $EC_{50}$ (nM) | 47 | 75 | 76 | 24 | 58 | 48 | 356 | 37 |
| Mouse Glucokinase Ymax (maximal activation) | 209% | 206% | 186% | 202% | 191% | 176% | 245 | 194% |
| CYP450 1A2 $IC_{50}$ (μM) | >40 | >40 | >40 | >40 | >40 | >6.7 | 20 | >40 |
| CYP450 2C8 $IC_{50}$ (μM) | — | — | — | — | 20 | >6.7 | 17.6 | 24.6 |
| CYP450 2C9 $IC_{50}$ (μM) | 6.1 | 8.5 | 11 | 1.0 | 4.02 | >6.7 | 20 | 26.8 |
| CYP450 2C19 $IC_{50}$ (μM) | 29.5 | 32.5 | >40 | 0.6 | 14.6 | >20.0 | 20 | >40 |
| CYP450 2D6 $IC_{50}$ (μM) | >40 | >40 | >40 | >40 | >40 | >6.7 | 20 | >40 |
| CYP450 3A4 $IC_{50}$ (μM) | 27.8 | >40 | >40 | >40 | >40 | >6.7 | 20 | >40 |
| Metabolic Stability Human Liver Microsomes (0.5 μM) | 4% | 54% | 80% | 26% | 70% | 100% | 96% | 80% |
| Metabolic Stability Mouse (0.5 μM) | 72% | 90% | 96% | 64% | 86% | 100% | 92% | 92% |
| Aqueous Solubility (μg/mL) | 16 | 9 | 65 | — | 4 | 730 | — | 74 |

In Vivo Studies: Oral Glucose Tolerance Test (OGTT)

Oral glucose tolerance tests were carried out on male DIO (diet-induced obese) C57BL/6J mice fed a high fat diet (60% kcal from fat) for 26 weeks prior to experimentation. Mice were fasted overnight before use for experiments. A test compound or vehicle (either: 1) 40% PEG 400+10% Cremophore+50% water or 2) 10% dimethyl acetamide+ 10% ethanol+10% Cremophore+70% water) was given orally 60 min before oral administration of a glucose solution at a dose of 2 g/kg body weight (oral glucose tolerance test; OGTT). Blood glucose levels were measured from tail-bled samples taken at different time points before and after administration of glucose (time course of 2 hours). A time curve of the blood glucose was generated and the change from baseline area-under-the curve (ΔAUC) from 0-120 min was calculated (the time glucose administration being time zero).

Find below in Table 2 data for compared compounds (See WO 2008/005964 A1 and WO 2009/041475 A1). The comparative data shows the unexpected reduction in glucose AUC levels in an OGTT test in DIO mice as described above.

TABLE 2

Comparative In vivo Data

| C57/B16J Mice | EX. 37 WO 2008/005964 A1 | EX. 54 WO 2008/005964 A1 | EX. 83 WO 2008/005964 A1 | EX. 137 WO 2008/005964 A1 | EX. 169 WO 2008/005964 A1 | EX. 117 U.S. Pat. No. 7,432,287 | EX. 48 U.S. Pat. No. 7,977,367 | EX. 48 U.S. Pat. No. 7,977,367 | Ex. 1 Instant application |
|---|---|---|---|---|---|---|---|---|---|
| Dose | 10 mg/kg = 16 μmol/kg | 10 mg/kg = 17 μmol/kg | 10 μmol/kg | 30 μmol/kg | 10 μmol/kg | 10 μmol/kg | 10 μmol/kg | 30 μmol/kg | 10 μmol/kg |
| Glucose lowering (30 min) | ND | ND | ND | ND | No significant lowering | Significant lowering | No significant lowering | Significant lowering | Significant lowering |
| Glucose lowering (60 min) | ND | ND | ND | ND | No significant lowering | Significant lowering | Significant lowering | Significant lowering | Significant lowering |
| Glucose lowering (120 min) | ND | ND | ND | ND | No significant lowering | Significant lowering | No significant lowering | No significant lowering | Significant lowering |
| Glucose lowering (AUC) (120 min) | −77% (Statistically significant) P <0.001 | −50% (Statistically significant) P <0.001 | −39% (Statistically significant) P <0.001 | −48% (not statistically significant) | −8% (not statistically significant) | −67% (Statistically significant) P <0.001 | −20% (not statistically significant) | −43% (Statistically significant) P <0.001 | −47% (Statistically significant) P <0.001 |
| Insulin Increase | No significant Increase @ 10 mpk; Significant increase @ 30 mpk | No significant increase @ 10 or 30 mg/kg | No significant increase @ 10 or 30 μmol/kg | No significant increase @ 30 μmol/kg | No significant increase @ 10 μmol/kg | Significant Increase @ doses ≥3 μmol/kg | No significant increase up to 300 μmol/kg | No significant increase up to 300 μmol/kg | No significant increase up to 300 μmol/kg |

In Vivo Studies: Pharmacokinetic Study

Pharmacokinetic (PK) screening studies were carried out by methods known to one of ordinary skill in the art. For example, study compounds were administered orally to male C57 Black6j (C57B16J) mice (N=3 per time point) at 10 mg/kg as solutions in a PEG400/Cremphor EL/water (40/10/50) vehicle. The mice were fasted overnight prior to the PK study. Blood samples were taken at 0.5, 1, 2, and 4 hr post dose by cardiac bleeding. Blood samples (~0.2 mL) were added with $K_2EDTA$ and centrifuged at 4° C. (1500-2000×g) to obtain plasma. Liver samples (N=3) were collected at 1 hr post dose. The liver tissues were homogenized with 3 volumes of water to form uniform homogenates. Both plasma and liver samples were stored at −20° C. before they were analyzed by LC/MS/MS. The plasma AUC were calculated using linear and log trapezoidal summations. The liver-to-plasma (L/P) ratio was calculated by dividing the total concentration in liver with plasma concentrations for respective mice. The average of L/P ratios from 3 mice was reported together with the standard deviation.

Find below in Table 3 data for compared compounds (See WO 2008/005964 A1 and WO 2009/041475 A1). The comparative data shows the unexpected significant liver selectivity of the compounds of the present invention.

TABLE 3

Comparative PK Data

| C57/B16J Mice | EX. 37 WO 2008/005964 A1 | EX. 54 WO 2008/005964 A1 | EX. 83 WO 2008/005964 A1 | EX. 137 WO 2008/005964 A1 | EX. 169 WO 2008/005964 A1 | EX. 117 U.S. Pat. No. 7,432,287 | EX. 48 U.S. Pat. No. 7,977,367 | Ex. 1 Instant application |
|---|---|---|---|---|---|---|---|---|
| Dose | 10 mg/kg | 10 mg/kg | 10 mg/kg | 10 mg/kg | 10 mg/kg | 10 mg/kg | 10 mg/kg | 10 mg/kg |
| Plasma (0.5 hr) | 6845 ± 2596 nM | 435 ± 100 nM | 1261 ± 375 nM | 1876 ± 302 nM | 118 ± 29 nM | 23193 ± 13418 nM | 7285 ± 856 nM | 604 ± 234 nM |
| Plasma (1 hr) | 17162 ± 8590 nM | 571 ± 18 nM | 1140 ± 331 nM | 1542 ± 544 nM | 115 ± 11 nM | 20062 ± 4027 nM | 10115 ± 1085 nM | 631 ± 286 nM |
| Plasma (2 hr) | 7822 ± 2008 nM | 467 ± 49 nM | 311 ± 217 nM | 754 ± 210 nM | 95 ± 10 nM | 7031 ± 1179 nM | 13120 ± 6756 nM | 398 ± 193 nM |
| Plasma (4 hr) | 2485 ± 1360 nM | 485 ± 290 nM | 302 ± 266 nM | 214 ± 107 nM | 48 ± 18 nM | 1699 ± 28 nM | 6712 ± 2591 nM | 193 ± 133 nM |
| Plasma AUC(4 hr) | 12144 nM · hr (24 hr) | 4210 nM · hr | 2166 nM · hr | 3280 nM · hr | 330 nM · hr | 36530 nM · hr | 36910 nM · hr | 1532 nM · hr |
| Liver (1 hr) | 38570 ± 11946 nM | 9680 ± 351 nM | 3325 ± 500 nM (4 hr) | 51339 ± 8802 nM | 1608 ± 345 nM | 22242 ± 6183 nM | 19816 ± 7328 nM | 21626 ± 1359 nM |
| Liver/Plasma ratio | 2.2 | 16.9 | 16.2 | 36.8 | 13.9 | 1.1 | 1.9 | 39 |

For additional PK studies, prodrug example compounds were dosed in rats (the general procedure was carried out as described above for the mouse PK studies) as solutions (40% PEG400+10% Cremaphore+50% water) at 10 mg/kg, and blood samples were taken at 0.25, 0.5, 1, 2, 4, 6, and 8 hr post dose. Find below in Table 4 data for prodrug compounds of the present invention. The data shows the unexpected significant liver selectivity of the compounds of the present invention.

TABLE 4

PK Data

| Sprague/Dawley Rats | Example 1 | Example 6 | Example 8 |
|---|---|---|---|
| Dose | 10 mg/kg | 10 mg/kg | 10 mg/kg |
| Plasma (0.25 hr) | 251 ± 269 nM | 573 ± 134 nM | 419 ± 15 nM |
| Plasma (0.5 hr) | 233 ± 72 nM | 764 ± 137 nM | 650 ± 174 nM |
| Plasma (1 hr) | 429 ± 58 nM | 1068 ± 341 nM | 824 ± 165 nM |
| Plasma (2 hr) | 180 ± 15 nM | 353 ± 193 nM | 202 ± 52 nM |
| Plasma (4 hr) | 54 ± 15 nM | 47 ± 18 nM | 35 ± 4 nM |
| Plasma (6 hr) | 10 ± 6 nM | 5 ± 2 nM | 6 ± 1 nM |
| Plasma (8 hr) | 7 ± 3 nM | 4 ± 1 nM | 10 nM |
| Plasma AUC (0-8 hr) | 815 ± 68 nM * h | 1686 ± 433 nM * h | 1211 ± 80 nM * h |

Surprisingly, it was discovered that the compound of the present invention possesses beneficial pharmacological characteristics, such as, the combination of liver selectivity, improved glucose reduction at lower dosage levels, improved solubility and decreased cytochrome P450 enzyme inhibition or induction in comparison to compounds known in the art. See Tables 1, 2, 3 and 4. For example, Example 1 of the present invention and Example 169 of WO 2008/005964 A1. Example 1 of the present invention has: 1) a $EC_{50}$ of 36 nM at human GK, 2) a CYP450 2C9 $IC_{50}$ of 26.8 µM, 3) an aqueous solubility of 74 µg/mL, 4) a reduction in glucose AUC (after an oral glucose tolerance test [OGTT] in diet-induced obese mice) at a 10 µmol/kg dose of 47%, and 5) 1 hour after administration of a 10 mg/kg dose in male C57B16J mice, liver exposure of 21626±1359 nM and a liver:plasma ratio of ~39:1. In comparison, Example 169 of WO 2008/005964 A1 while having similar activity against GK (a GK $EC_{50}$ of 54 nM) is 6 times more potent against CYP450 2C9 (a CYP450 2C9 $IC_{50}$ of 4.02 µM), 18 times less soluble (an aqueous solubility of 4 µg/mL), six times less effective in reducing glucose AUC after an oral glucose tolerance test in diet-induced obese mice (a reduction in glucose AUC at 10 µmol/kg of 8%), and gives ~13-fold less drug exposure in the liver (1608±345 nM after 1 hour of a 10 mg/kg dose administered to male C57B16J mice) and an ~3-fold decreased liver:plasma selectivity (13.9:1 vs. 39:1)

UTILITIES AND COMBINATIONS

A. Utilities

The compounds of the present invention possess activity as enhancers of activity of the enzyme glucokinase, and, therefore, may be used in the treatment of diseases associated with glucokinase activity.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, and other maladies. Consequently, it is believed that the compounds of the present invention may be used in preventing, inhibiting, or treating diabetes, especially Type II diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy, and glaucoma.

Metabolic Syndrome or "Syndrome X" is described in Ford et al., *J. Am. Med. Assoc.*, 287:356-359 (2002) and Arbeeny et al., *Curr. Med. Chem.-Imm., Endoc. & Metab. Agents*, 1:1-24 (2001).

B. Combinations

The present invention includes within its scope pharmaceutical compositions comprising, as an active ingredient, a therapeutically effective amount of the compound of the present invention in combination with a pharmaceutical carrier or diluent. Optionally, the compound of the present invention can be used in combination with one or more other therapeutic agent(s), e.g., an antidiabetic agent or other pharmaceutically active material.

The compound of the present invention may be employed in combination with one or more other suitable therapeutic agents useful in the treatment of the aforementioned disorders including: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, appetite suppressants, treatments for heart failure, treatments for peripheral arterial disease and anti-inflammatory agents.

Examples of suitable anti-diabetic agents for use in combination with the compound of the present invention include insulin and insulin analogs (e.g., LysPro insulin, inhaled formulations comprising insulin); glucagon-like peptides; sulfonylureas and analogs (e.g., chlorpropamide, glibenclamide, tolbutamide, tolazamide, acetohexamide, glypizide, glyburide, glimepiride, repaglinide, meglitinide); biguanides (e.g., metformin, phenformin, buformin); alpha2-antagonists and imidazolines (e.g., midaglizole, isaglidole, deriglidole, idazoxan, efaroxan, fluparoxan); other insulin secretagogues (e.g., linogliride, insulinotropin, exendin-4, N,N-dimethyl-N'-[2-(4-morpholinyl)phenyl]guanidine (E)-2-butenedioate salt (BTS-675820), (−)-N-(trans-4-isopropylcyclohexanecarbonyl)-D-phenylalanine (A-4166)); thiazolidinediones and PPAR-gamma agonists (e.g., ciglitazone, pioglitazone, troglitazone, rosiglitazone); PPAR-alpha agonists e.g., fenofibrate, gemfibrozil); PPAR alpha/gamma dual agonists (e.g., muraglitazar, peliglitazar, aleglitazar); SGLT2 inhibitors (e.g., 3-(benzo[b]furan-5-yl)-2',6'-dihydroxy-4'-methylpropiophenone-2'-O-(6-O-methoxycarbonyl)-β-d-glucopyranoside (T-1095 Tanabe Seiyaku), phlorizin, TS-033 (Taisho), dapagliflozin (BMS), sergiflozin (Kissei), AVE 2268 (Sanofi-Aventis)), canagliflozin; 11-beta-hydroxysteriod dehydrogenase type I inhibitors (e.g., AMG221, INCB13739); dipeptidyl peptidase-IV (DPP4) inhibitors (e.g., saxagliptin, sitagliptin, vildagliptin, alogliptin and denagliptin); glucagon-like peptide-1 (GLP-1) receptor agonists (e.g., Exenatide (Byetta), NN2211 (Liraglutide, Novo Nordisk), AVE0010 (Sanofi-Aventis), R1583 (Roche/Ipsen), SUN E7001 (Daiichi/Santory), GSK-716155 (GSK/Human Genome Sciences) and Exendin-4 (PC-DACTM); aldose reductase inhibitors (e.g., those disclosed in WO 99/26659); RXR agonists (e.g., reglitazar (JTT-501), 5-[[6-[(2-fluorophenyl)methoxy]-2-naphthalenyl]methyl]-2,4-thiazolidinedione (MCC-555), 5-[[3-(5,6,7,8-tetrahydro-3,5,5,8,8-pentamethyl-2-naphthalenyl)-4-(trifluoromethoxy)phenyl]methylene]-2,4-thiazolidinedione (MX-6054), DRF2593, farglitazar, (±)-5-[(2,4-dioxothiazolidin-5-yl)methyl]-2-methoxy-N-[[(4-trifluoromethyl)phenyl]methyl]benzamide (KRP-297), 6-[1-(5,6,7,8-tetrahydro-3,5,5,8,8-pentamethyl-2-naphthalenyl)cyclopropyl]-3-pyridinecarboxylic acid (LG100268)); fatty acid oxidation inhibitors (e.g., clomoxir, etomoxir; α-glucosidase inhibitors: precose, acarbose, miglitol, emiglitate, voglibose, 2,6-dideoxy-2,6-imino-7-O-β-D-glucopyranosyl-D-glycero-L-gulo-heptitol (MDL-25,637), camiglibose); beta-agonists (e.g., methyl ester [4-[(2R)-2-[[(2R)-2-(3-chlorophenyl)-2-hydroxyethyl]amino]propyl]phenoxy]-acetic acid (BRL 35135), 2-[4-[(2S)-2-[[(2S)-2-(3-chlorophenyl)-2-hydroxyethyl]amino]propyl]phenoxy]-acetic acid (BRL 37344), 4-[(3R)-3-[bis[(2R)-2-hydroxy-2-phenylethyl]amino]butyl]-benzamide (Ro 16-8714), 2-[4-[2-[[(2S)-2-hydroxy-3-phenoxypropyl]amino]ethoxy]phenoxy]-N-(2-methoxyethyl)-acetamide (ICI D7114), 5-[(2R)-2-[[(2R)-2-(3-chlorophenyl)-2-hydroxyethyl]amino]propyl]-3-benzodioxole-2,2-dicarboxylic acid, disodium salt (CL 316, 243), TAK-667, AZ40140); phosphodiesterase inhibitors, both cAMP and cGMP type (e.g., sildenafil, 9-((1S,2R)-2-fluoro-1-methylpropyl)-2-methoxy-6-(1-piperazinyl)purine hydrochloride (L-686398), L-386,398); amylin agonists (e.g., pramlintide); lipoxygenase inhibitors (e.g., masoprocal); somatostatin analogs (e.g., lanreotide, seglitide, octreotide); glucagon antagonists (e.g., BAY 276-9955); insulin signaling agonists, insulin mimetics, PTP1B inhibitors (e.g., 2-[2-(1,1-dimethyl-2-propenyl)-1H-indol-3-yl]-3,6-dihydroxy-5-[7-(3-methyl-2-butenyl)-1H-indol-3-yl]-2,5-cyclohexadiene-1,4-dione (L-783281), TER17411, TER17529); gluconeogenesis inhibitors (e.g., GP3034); somatostatin analogs and antagonists; antipolytic agents (e.g., nicotinic acid, acipimox, N-cyclohexyl-2'-O-methyl-adenosine (WAG 994)); glucose transport stimulating agents (e.g., 4-chloro-α-[(4-methylphenyl)sulfonyl]-benzeneheptanoic acid (BM-130795)); glucose synthase kinase inhibitors (e.g., lithium chloride, CT98014, CT98023); galanin receptor agonists; Chemokine receptor antagonist CCR2/5 (e.g., NCB3284, MK-0812, INCB8696, maraviroc (Pfizer) and vicriviroc); thyroid receptor agonists (e.g., KB-2115 (Karo-Bio)); glucokinase activators (e.g., RO-27-4375, RO-28-1675 (Roche), 6-[[3-[(1S)-2-methoxy-1-methylethoxy]-5-[(1S)-1-methyl-2-phenylethoxy]benzoyl]amino]-3-pyridinecarboxylic acid (GKA-50 AstraZeneca)); GPR 40 modulators (e.g., (S)-4-(dimethylamino)-3-(4-((4-methyl-2-p-tolylthiazol-5-yl)methoxy)phenyl)-4-oxobutanoic acid, 6-chloro-2-(4-chlorobenzylthio)-1-(4-(methoxymethoxy) phenyl)-1H-benzo[d]imidazole, TAK-875, CNX011, and P1736) and GPR-119 modulators (e.g., PSN821 (OSI Pharmaceuticals)).

Examples of suitable lipid lowering agents and anti-atherosclerotic agents for use in combination with the compound of the present invention include one or more MTP/ApoB secretion inhibitors (e.g., dirlopatide, N-(2,2,2-trifluoroethyl)-9-[4-[4-[[[4'-(trifluoromethyl)[1,1'-biphenyl]-2-yl]carbonyl-]amino]-1-piperidinyl]butyl]-9H-fluorene-9-carboxamide, methanesulfonate, CP-741952 (Pfizer), SLx-4090 (Surface Logix)); HMG CoA reductase inhibitors (e.g., atorvastatin, rosuvastatin, simvastatin, pravastatin, lovastatin, fluvastatin); squalene synthetase inhibitors, PPAR alpha agonists and fibric acid derivatives (e.g., fenofibrate, gemfibrozil); ACAT inhibitors; lipoxygenase inhibitors; cholesterol absorption inhibitors (e.g., ezetimibe); thyroid receptor agonists (e.g., as set forth above); Ileal Na+/bile acid co-transporter inhibitors (e.g., compounds as disclosed in *Drugs of the Future*, 24:425-430 (1999); upregulators of LDL receptor activity (e.g., (3R)-3-[(13R)-13-hydroxy-10-oxotetradecyl]-5,7-dimethoxy-1 (3H)-isobenzofuranone (Taisho Pharmaceutical Co. Ltd.) and (3α,4α,5α)-4-(2-propenyl)-cholestan-3-ol (Eli Lilly); bile acid sequestrants (e.g., WELCHOL®, COLESTID®, LoCholest and QUESTRAN®; and fibric acid derivatives, such as Atromid, LOPID® and Tricot); cholesterol ester transfer protein inhibitors (e.g., torcetrapib and (2R)-3-{[3-(4-chloro-3-ethyl-phenoxy)-phenyl]-[[3-(1,1,2,2-tetrafluoroethoxy)phenyl]methyl]amino}-1,1,1-trifluoro-2-propanol); nicotinic acid and derivatives thereof (e.g., niacin, acipimox); PCSK9 inhibitors; LXR agonists (e.g., those disclosed in U.S. Patent Application Publication Nos. 2003/01814206, 2005/0080111, and 2005/0245515); lipoxygenase inhibitors (e.g., such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al., "Attenuation of diet-induced atherosclerosis in rabbits with a highly selective 15-lipoxygenase inhibitor lacking significant antioxidant properties", *Brit. J. Pharmacology*, 120:1199-1206 (1997), and Cornicelli et al., "15-Lipoxygenase and its Inhibition: A Novel Therapeutic Target for Vascular Disease", *Current Pharmaceutical Design*, 5:11-20 (1999)).

Preferred hypolipidemic agents are pravastatin, lovastatin, simvastatin, atorvastatin, fluvastatin, cerivastatin, atavastatin, and rosuvastatin.

Examples of suitable anti-hypertensive agents for use in combination with the compound of the present invention include beta adrenergic blockers, calcium channel blockers (L-type and T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors (e.g., aliskiren), ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan, and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopeptidase inhibitors (dual NEP-ACE inhibitors) (e.g., omapatrilat and gemopatrilat), nitrates, central alpha agonists (e.g., clonidine), alpha1 blockers (e.g., prazosine), arterial vasodilators (e.g., minoxidil), sympatolytics (e.g., resperine), renin inhibitors (e.g., Aliskiren (Novartis)).

Examples of suitable anti-obesity agents for use in combination with the compound of the present invention include a cannabinoid receptor 1 antagonist or inverse agonist (e.g., rimonabant, (4S)-3-(4-chlorophenyl)-N-[(4-chlorophenyl) sulfonyl]-4,5-dihydro-N'-methyl-4-phenyl-1H-pyrazole-1-carboximidamide (SLV 319), CP-945598 (Pfizer), Surinabant (SR-147778, Sanofi-Aventis), N-[(1S,2S)-3-(4-chlorophenyl)-2-(3-cyanophenyl)-1-methylpropyl]-2-methyl-2-{[5-(trifluoromethyl)pyridin-2-yl] oxy}propanamide (Merck) and those discussed in Hertzog, D. L., *Expert Opin. Ther. Patents,* 14:1435-1452 (2004)); a beta 3 adrenergic agonist (e.g., rafabegron (AJ9677, Takeda/ Dainippon), N-[4-[2-[[(2S)-3-[(6-amino-3-pyridinyl)oxy]-2-hydroxypropyl]amino]ethyl]phenyl]-4-(1-methylethyl)-benzenesulfonamide (L750355, Merck), or CP331648 (Pfizer,) or other known beta 3 agonists, as disclosed in U.S. Pat. Nos. 5,541,204, 5,770,615, 5,491,134, 5,776,983, and 5,488,064, with rafabegron, N-[4-[2-[[(2S)-3-[(6-amino-3-pyridinyl)oxy]-2-hydroxypropyl]amino]ethyl]phenyl]-4-(1-methylethyl)-benzenesulfonamide, and CP331648 being preferred); a lipase inhibitor (e.g., orlistat or cetilistat, with orlistat being preferred); a serotonin and norepinephrine reuptake inhibitor (e.g., sibutramine, Abbott and tesofensine, Neurosearch) with sibutramine being preferred; a dopamine reuptake inhibitor (e.g., buproprion, GSK); or 5-HT$_{2C}$ agonist, (e.g., lorcaserin hydrochloride (Arena), WAY-163909 [(7bR,10aR)-1,2,3,4,8,9,10,10a-octahydro-7bH-cyclopenta-[b][1,4]diazepino[6,7,1hi]indole], with lorcaserin hydrochloride being preferred); 5-HT6 receptor antagonists (Suven, Biovitrum, Epix), anti-epileptics topiramate (Johnson & Johnson) and zonisamide, a ciliary neurotrophic factor agonist (e.g., AXOKINE® (Regeneron); brain-derived neurotrophic factor (BDNF), orexin antagonists, histamine receptor-3 (H3) modulators, melanin-concentrating hormone receptor (MCHR) antagonists (e.g., GSK-856464 (GlaxoSmithKline), T-0910792 (Amgen)); diacylglycerol acyltransferase (DGAT) inhibitors (e.g., BAY-74-4113 (Bayer), PF-04620110, and LCQ908); acetyl-CoA carboxylase (ACC) inhibitors (e.g., N-(4-(4-(4-isopropoxyphenoxy) phenyl)but-3-yn-2-yl)acetamide (A-80040, Abbott), (R)-anthracen-9-yl(3-(morpholine-4-carbonyl)-1,4'-bipiperidin-1'-yl)methanone (CP-640186, Pfizer)); SCD-1 inhibitors as described by Jiang et al., *Diabetes,* 53 (2004), (abs 653-p); amylin receptor agonists (e.g., compounds disclosed in WO 2005/025504); thyroid receptor agonists (e.g., as set forth above); growth hormone secretagogue receptor (GHSR) antagonists (e.g., A-778193 (Abbott), leptin and leptin mimetics (e.g., OB-3 (Aegis/Albany Medical College), leptin analogs A-100 and A-200 (Amgen), CBT-001452 (Cambridge Biotechnology), ML-22952 (Millennium)), PYY receptor agonist (e.g., AC-162352 (Amylin), PYY-3-36 (Emishere), PYY(3-36)NH2 (Unigene)), NPY-Y4 agonists (7TM Pharma WO 2005/089786 (A2,A3)-1), NPY-5 antagonists (e.g., NPY5RA-972 (AstraZeneca), GW-594884A (GlaxoSmithKline), J-104870 (Banyu)); MTP/apoB secretion inhibitors (as set forth above), and/or an anorectic agent.

The anorectic agent which may be optionally employed in combination with compound of the present invention include dexamphetamine, phentermine, phenylpropanolamine, or mazindol, with dexamphetamine being preferred.

Other compounds that can be used in combination with the compound of the present invention include CCK receptor agonists (e.g., SR-27895B); galanin receptor antagonists; MCR-4 antagonists (e.g., N-acetyl-L-norleucyl-L-glutaminyl-L-histidyl-D-phenylalanyl-L-arginyl-D-tryptophyl-glycinamide, (HP-228); urocortin mimetics, CRF antagonists, and CRF binding proteins (e.g., mifepristone (RU-486), urocortin).

Further, the compound of the present invention may be used in combination with HIV protease inhibitors, including but not limited to REYATAZ® and KALETRA®.

Examples of suitable memory enhancing agents, anti-dementia agents, or cognition promoting agents for use in combination with the compound of the present invention include, but are not limited to ARICEPT®, razadyne, donepezil, rivastigmine, galantamine, memantine, tacrine, metrifonate, muscarine, xanomelline, deprenyl and physostigmine.

Examples of suitable anti-inflammatory agents for use in combination with the compound of the present invention include, but are not limited to, NSAIDS, prednisone, acetaminophen, aspirin, codeine, fentanyl, ibuprofen, indomethacin, ketorolac, morphine, naproxen, phenacetin, piroxicam, sufentanyl, sunlindac, interferon alpha, prednisolone, methylprednisolone, dexamethazone, flucatisone, betamethasone, hydrocortisone, beclomethasone, REMICADE®, ORENCIA®, and ENBREL®.

The aforementioned patents and patent applications are incorporated herein by reference.

The above other therapeutic agents, when employed in combination with the compound of the present invention may be used, for example, in those amounts indicated in the *Physicians' Desk Reference*, as in the patents set out above, or as otherwise determined by one of ordinary skill in the art.

Dosage and Formulation

The compound of this disclosure can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compound of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disorder.

By way of general guidance, the daily oral dosage of each active ingredient, when used for the indicated effects, will range between about 0.001 to 1000 mg/kg of body weight, or between about 0.01 to 100 mg/kg of body weight per day, or alternatively, between about 1.0 to 20 mg/kg/day. The compound of this invention may be administered in a single daily dose, or the total daily dosage may be administered in divided doses of two, three, or four times daily. In one embodiment, the daily oral dosage of the active ingredient is between 3 and 600 mg either administered once daily or in divided doses administered twice daily. Alternatively, the active ingredient may be administered in doses of 10-20 mg administered twice daily or 40 to 100 mg administered once daily. Alternatively, the active ingredient may be administered a dose of 12.5 mg twice a day or 75 mg once a day. Alternatively, the active ingredient may be administered in doses of 3, 10, 30, 100, 300, and 600 mg administered either once or twice a day.

The compound of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compound is typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compound of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compound of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compound of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Dispersion

A spray dried dispersion can be prepared for oral administration by methods know to one skilled in the art.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where two or more of the foregoing second therapeutic agents are administered with the compound of the examples, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the examples and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

What is claimed is:

1. A compound, enantiomer, prodrug, diastereomer, or salt thereof, that is

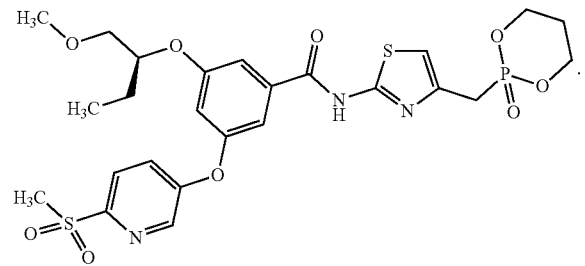 [SMILES: CC[C@@H](COC)Oc1cc(Oc2ccc(S(C)(=O)=O)nc2)cc(C(=O)Nc2nc(CP3(=O)OCCCO3)cs2)c1]

2. The compound of claim 1, wherein the compound is a salt of the compound.

3. The compound of claim 1, wherein the compound is the sodium or potassium salt.

4. The compound of claim 1, wherein the compound is the sodium salt.

5. The compound of claim 1, wherein the compound is the potassium salt.

6. The compound of claim 1 that is a crystalline form of said compound.

7. The compound of claim 6, wherein the crystalline form is the N-1 or P-2 form.

8. The compound of claim 6, wherein the crystalline form is the N-1 form.

9. The compound of claim 8, wherein the crystalline form is in substantially pure form.

10. The compound of claim 8, wherein the crystalline form of the compound is characterized by unit cell parameters substantially equal to the following:

Cell dimensions:

a=8.0531(2)

b=13.5078(3)

c=13.7063(3)

α=73.091(1)

β=88.186(1)

γ=89.881(1)

Space group: P1

Molecules/asymmetric unit (Z'): 2.

11. A compound, enantiomer, diastereomer, or salt thereof, selected from the group consisting of:

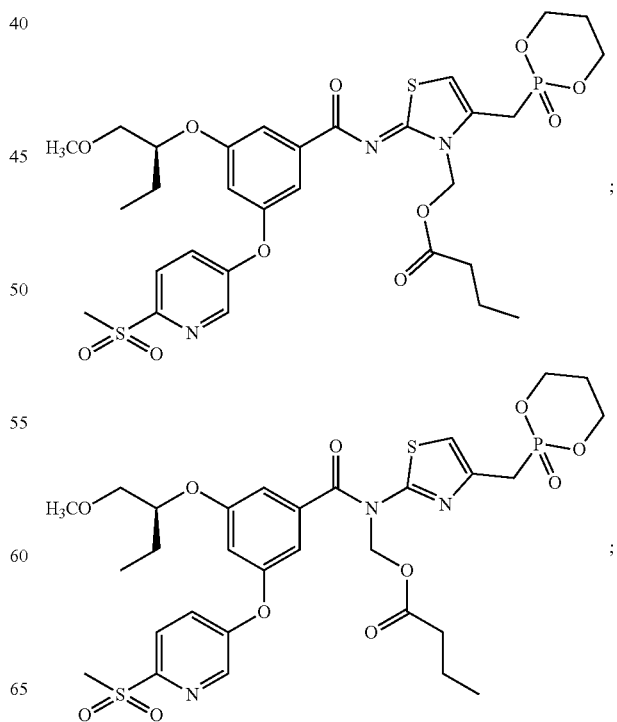

-continued

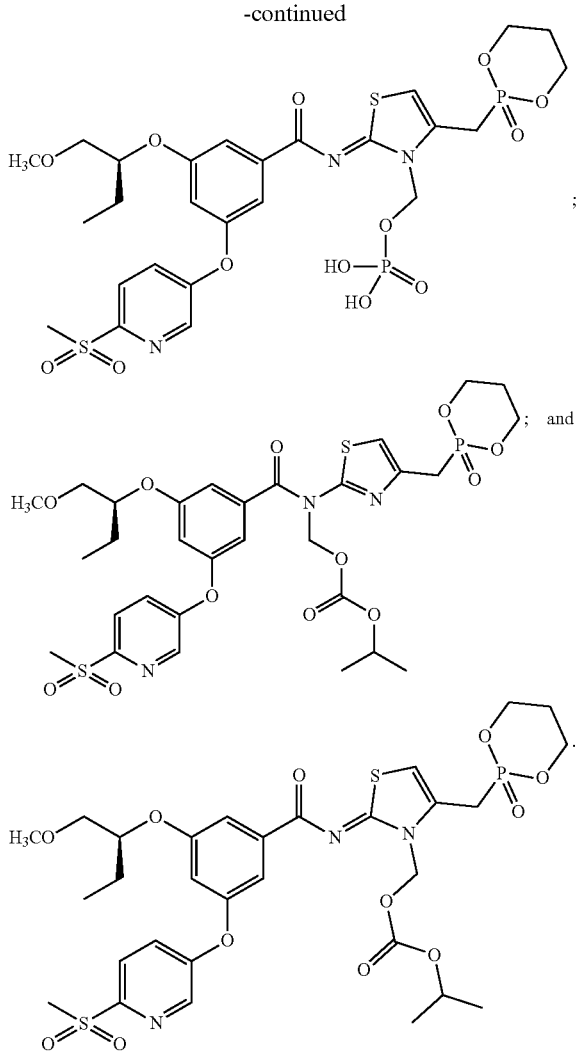

12. A pharmaceutical composition comprising a compound as defined in claim 1 or a pharmaceutically-acceptable salt thereof and a pharmaceutically acceptable carrier thereof.

13. A method for treating a disease or disorder comprising administering a therapeutically effective amount of a compound of claim 1 or a pharmaceutically-acceptable salt thereof, to a human patient in need thereof, wherein said disease or disorder is diabetes, hyperglycemia, impaired glucose tolerance, insulin resistance, or hyperinsulinemia.

14. A pharmaceutical composition comprising a compound as defined in claim 4, wherein said compound is the sodium salt; and a pharmaceutically acceptable carrier thereof.

15. A pharmaceutical composition comprising a compound as defined in claim 5, wherein said compound is the potassium salt; and a pharmaceutically acceptable carrier thereof.

16. A pharmaceutical composition comprising a compound as defined in claim 8; and a pharmaceutically acceptable carrier thereof.

17. The method according to claim 13, wherein said compound is the crystalline N-1 form.

18. The method according to claim 13, wherein said compound is the sodium salt.

19. The method according to claim 13, wherein said compound is the potassium salt.

* * * * *

UNITED STATES PATENT AND TRADEMARK OFFICE
CERTIFICATE OF CORRECTION

PATENT NO. : 10,604,541 B2
APPLICATION NO. : 16/318173
DATED : March 31, 2020
INVENTOR(S) : Cheng et al.

Page 1 of 1

It is certified that error appears in the above-identified patent and that said Letters Patent is hereby corrected as shown below:

On the Title Page

Item (57), Column 2, (Abstract), Line 3, after "in" delete "as".

In the Claims

In Column 54, Line 3, Claim 12, after "thereof" insert -- ; --.

Signed and Sealed this
Eleventh Day of August, 2020

Andrei Iancu
*Director of the United States Patent and Trademark Office*